(12) United States Patent
Tachdjian et al.

(10) Patent No.: US 7,265,139 B2
(45) Date of Patent: Sep. 4, 2007

(54) RXR ACTIVATING MOLECULES

(75) Inventors: Catherine Tachdjian, San Diego, CA (US); Karine Jakubowicz-Jaillardon, San Diego, CA (US)

(73) Assignees: Incyte San Diego Inc., Wilmington, DE (US); Ortho McNeil Pharmaceutical Inc., Rariton, NJ (US)

( * ) Notice: Subject to any disclaimer, the term of this patent is extended or adjusted under 35 U.S.C. 154(b) by 164 days.

(21) Appl. No.: 10/098,184

(22) Filed: Mar. 8, 2002

(65) Prior Publication Data
US 2003/0105333 A1 Jun. 5, 2003

Related U.S. Application Data

(60) Provisional application No. 60/274,342, filed on Mar. 8, 2001.

(51) Int. Cl.
C07D 277/34 (2006.01)
A61K 31/425 (2006.01)

(52) U.S. Cl. ........................................ 514/369; 548/183
(58) Field of Classification Search ................. 548/183; 514/369
See application file for complete search history.

(56) References Cited

U.S. PATENT DOCUMENTS

| | | | |
|---|---|---|---|
| 4,051,842 A | 10/1977 | Hazel et al. | |
| 4,140,122 A | 2/1979 | Kühl et al. | |
| 4,383,529 A | 5/1983 | Webster | |
| 4,668,506 A | 5/1987 | Bawa | |
| 4,713,244 A | 12/1987 | Bawa et al. | |
| 4,788,063 A | 11/1988 | Fisher et al. | |
| 4,824,833 A | 4/1989 | Iijima et al. | |
| 4,897,393 A | 1/1990 | Iijima et al. | |
| 4,931,279 A | 6/1990 | Bawa et al. | |
| 4,948,900 A | 8/1990 | Iijima et al. | |
| 4,971,996 A | 11/1990 | Shiraishi et al. | |
| 5,223,522 A | 6/1993 | Clark et al. | |
| 5,330,998 A | 7/1994 | Clark et al. | |
| 5,512,689 A | 4/1996 | Quallich | |
| 5,523,314 A | 6/1996 | Bue-Valleskey et al. | |

(Continued)

FOREIGN PATENT DOCUMENTS

| EP | 0 212 617 | 3/1987 |
|---|---|---|
| EP | 0 304 493 | 3/1989 |
| EP | 0 3343 643 | 11/1989 |
| EP | 1 048 659 A1 | 11/2000 |
| EP | 1 142 885 | 10/2001 |
| JP | 55 038359 | 3/1980 |
| WO | WO 93/21146 | 10/1993 |
| WO | WO 94/12880 | 6/1994 |
| WO | WO 97/00249 | 1/1997 |
| WO | 97/00249 | 1/1997 |
| WO | WO 97/03682 | 2/1997 |
| WO | WO 97/27191 | 7/1997 |
| WO | WO 99/09965 | 3/1999 |
| WO | WO 99/24415 | 5/1999 |
| WO | 99/58127 | 11/1999 |
| WO | WO 99/58127 | 11/1999 |
| WO | 00/10573 | 3/2000 |
| WO | WO 00/18748 | 4/2000 |
| WO | WO 00/32598 | 6/2000 |
| WO | WO 02/071827 | 9/2000 |
| WO | 00/63196 | 10/2000 |
| WO | WO 00 66167 | 11/2000 |
| WO | WO 01/16122 | 3/2001 |
| WO | WO 01/16123 | 3/2001 |
| WO | WO 01/36402 | 5/2001 |
| WO | 02/12210 | 2/2002 |
| WO | WO 02/072009 | 9/2002 |
| WO | WO 02/072543 | 9/2002 |
| WO | 02/080935 A1 | 10/2002 |

OTHER PUBLICATIONS

Alley et al., "Feasibility of Drug Screening with Panels of Human Tumor Cell Lines Using a Microculture Tetrazolium Assay," Cancer Res. 48:589–601 (1988).

Amin et al., "Nitric Oxide Synthase and Cyclooxygenases: Distribution, Regulation, and Intervention in Arthritis," Nitric Pin. Rheumatol. 11(3):202–209 (1999).

Aranyos et al., "Novel Electron–Rich Bulky Phosphine Ligands Facilitate the Palladium–Catalyzed Preparation of Diaryl Ethers," J. Am. Chem. Soc. 121:4369–4378 (1999).

Armstrong et al., "Microchip Encoded Combinatorial Libraries: Generation of a Spatially Encoded Library from a Pool Synthesis," Medicinal Chemistry 50(6):258–260 (1996).

Askew et al., "Molecular Recognition with Convergent Function Groups. 6. Synthetic and Structural Studies with a Model Receptor for Nucleic Acid Components," J. Am. Chem. Soc. 111:1082–1090 (1989).

(Continued)

Primary Examiner—Kamal A. Saeed
(74) Attorney, Agent, or Firm—Needle & Rosenberg, P.C.

(57) ABSTRACT

The invention relates to molecules having Formula (100):

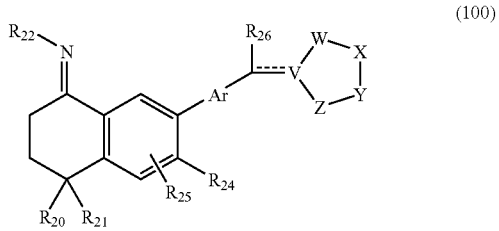

wherein ———— represents a bond present or absent; Ar is a substituted or unsubstituted benzene or pyridine ring; V is a C or N atom, and W, X, Y and Z together form a 2,4-thiazolidinedione, 2-thioxo-4-thiazolidinedione, isoxazolidinedione, 2,4-imidazolidinedione, [1,2,4]-oxadiazolidine-3,5-dione or 2-thioxo-4-imidazolidinedione residue; or a pharmaceutically acceptable salt thereof.

6 Claims, 17 Drawing Sheets

U.S. PATENT DOCUMENTS

| | | | |
|---|---|---|---|
| 5,565,324 A | 10/1996 | Still et al. | |
| 5,650,444 A | 7/1997 | Cagiano et al. | |
| 5,691,376 A | 11/1997 | Cagiano et al. | |
| 5,780,676 A | 7/1998 | Boehm et al. | |
| 6,060,596 A | 5/2000 | Lerner et al. | |
| 6,087,103 A | 7/2000 | Burmer | |
| 6,127,415 A | 10/2000 | Pfahl et al. | |
| 6,168,913 B1 | 1/2001 | Hochlowski et al. | |
| 6,262,044 B1 | 7/2001 | Møller et al. | |
| 6,765,013 B2 | 7/2004 | Pfahl et al. | |
| 6,927,228 B2 | 8/2005 | Bernardon et al. | |
| 2002/0143182 A1 | 10/2002 | Pfahl et al. | |
| 2003/0083357 A1 | 5/2003 | Pfahl et al. | |
| 2003/0105333 A1 | 6/2003 | Pfahl et al. | |
| 2003/0144329 A1 | 7/2003 | Pfahl et al. | |
| 2003/0153606 A1 | 8/2003 | Pfahl et al. | |
| 2003/0216432 A1 | 11/2003 | Pfahl et al. | |
| 2004/0034004 A1 | 2/2004 | Pfahl et al. | |
| 2004/0097566 A1 | 5/2004 | Pfahl et al. | |
| 2005/0014767 A1 | 1/2005 | Pfahl et al. | |
| 2005/0038098 A1 | 2/2005 | Tachdjian et al. | |
| 2005/0070581 A1 | 3/2005 | Pfahl et al. | |

OTHER PUBLICATIONS

Baldwin et al., "Synthesis of a Small Molecule Combinatorial Library Encoded with Molecular Tags," *J. Am. Chem. Soc.* 117:5588–5589 (1995).

Baraldi et al., "Exhaled Nitric Oxide Concentrations During Treatment of Wheezing Exacerbation in Infants and Young Children," Am. J. Respis. Crit. Care Med. 159(4 Pt. 1):1284–1288 (1999).

Beilstein Registry No. 29–30, 1975, Compound Registry No. 1120438.

Beilstien Registry No. 52, 1978, Compound Registry No. 4939128.

Black, "Simple Synthesis of 1-Azaadamantan-4-one," *Synthesis* 829–830 (1981).

Bradisher et al., "Aromatic Cyclodehydration XXIV. Cyclization of Derivatives of (2-biphenylly)pyruvic Acid," *J. Org. Chem.* 15(2):374–376 (1950).

Brand and Perrimon, "Target gene expression as a means of altering cell fates and generating dominant phenotypes," *Development* 118:401–415 (1993).

Bredt et al., "Isolation of Nitric Oxide Synthetase, a Calmodulin–Requiring Enzyme," *Proc. Natl. Acad. Sci.* 87:682–685 (1990).

Brennan et al., "Inhibitory Effect of TNFα Antibodies on Synovial Cell Interleukin–1 Production in Rheumatiod Arthritis," *Lancet* 2:244–247 (1989).

Brenner et al., "Encoded Combinatorial Chemistry," *Proc. Natl. Acad. Sci. USA* 89:5381–5383 (1992).

Chan et al., "New N–and O–Arylations with Phenloboronic Acids and Curpric Acetate," *Tetra. Lett.* 39:2933–2936 (1998).

Charpentier et al., "Synthesis, Structure—Affinity Relationships, and Biological Activities of Ligands Binding to Retinoic Acid Receptor Subtypes,"*J. Med. Chem.* 38:4993–5006 (1995).

Choi et al., "Similarity of Colorectal Cancer in Crohn's Disease and Ulcerative Colitis: Implications foe Carcinogenesis and Prevention," *Gut* 35:950–954 (1994).

Cobb et al., "N–(2–Benzolphenyl)–L–tyrosine PPAR Agonists. 3. Structure–Activity Relationship and Optimization of the N–Aryl Substituent," *J. Med. Chem.* 41:5055–5069 (1998).

Connolly, "Solvent–Accessible Surfaces of Proteins and Nucleic Acids," *Science* 221:709 (1983).

Darses et al., "Palladium–Catalyzed Cross–Coupling Reactions of Arenediazonium TetraFluoroborates with Aryl– and Alkenylboronic Acids," *Bull. Soc. Chem. Fr.* 133:1095–1102 (1996).

Ebisawa et al., "Novel Thiazolidinedione Derivatives with Retiniod Synergistic Activity," *Biol. Pharma. Bull.* 21(5):547–549 (1998).

Egea et al., "Crystal structure of the human RXRα ligand–binding domain bound to its natural ligand:9–cis retinoic acid," *EMBO J.* 19(11):2592–2601 (2000).

Evans et al., "Synthesis of Diaryl Ethers through the Copper–Promoted Arylation of Phenols with Arylboronic Acids. An Expedient Synthesis of Thyroxine," *Tetra. Lett.* 39:2937–2940 (1998).

Farahat et al., "Cytokine Expression in Synovial Membranes of Patients with Rheumatiod Arthritis and Osteoarthritis," *Ann. Rheum. Dis.* 52:870–875 (1993).

Ferrell, "Tripping the Switch Fantastic: How A Protein Kinase Casade Can Convert Graded Inputs in Switch–Like Outputs," *TIBS* 21:460–466 (1996).

Firooznia et al., "Enantioselective Synthesis of 4–Substituted Phenylalanines By Cross–Couples Reaction," *Tetra. Lett.* 40:213–216 (1999).

Förstermann et al., "Induced RAW 264.7 Macrophages Express Soluble and Particulate Nitric Oxide Synthase: Inhibition By Transforming Growth Factor–β," *Eur. J. Pharm.* 225:161–165 (1992).

Fukuto et al., "Inhibition Constitutive and Inducible Nitric Oxide Synthase: Potential Selective Inhibition," *Ann. Rev. Pharmacol. Oxicol.* 35:1665–194 (1995).

Gahtan et al., "Inflammatory Pathogenesis in Alheimer's Disease: Biological Mechanisms and Cognitive Sequeli," *Neurosci. Biobehav.* 23:615–633 (1999).

Glauser et al., "Pathogenesis and Potential Strategies for Prevention and Treatment of Septic Shock: An Update," *Clin. Infect. Dis.* 18(Suppl. 2):S205–216 (1994).

Haddach et al., "An New Method for the Synthesis of Ketones: The Palladium–Catalyzed Cross–Coupling of Acid Chlorides with Arlyboronic Acids," *Tetra. Lett.* 40:3109–3112 (1999).

Harris et al., "Localization of a Pioglitazone Response Element in the Adipocyte Fatty Acid–Binding Protein Gene," *Mol. Pharmacol.* 45:439–445 (1994).

Hudlicky, "Oxidations in Organic Chemistry," *ACS Monograph* 186:114–127 (1990).

Hudlicky, "Oxidations in organic Chemistry," *ACS Monograph* 186:133–149 (1990).

Indolese, "Suzuki–Type Coupling of Chloroarenes with Arylboronic Acdis Catalysed by nickel Complexes," *Tetra. Lett.* 38:3513–3516 (1997).

Ishiyama et al., "Palladium–Catalyzed Carbonylative Cross–Coupling Reaction of Arylboronic Acids with Aryl Electrophiles: Synthesis of Biaryl Ketones," *J. Org. Chem.* 63:4726–4731 (1998).

Ishiyama et al., "Palladium(0)–Catalyzed Cross–Coupling Reaction of Alkoxydiboron with Haloarenes: A Direct Procedure for Arylboronic Esters," *J. Org. Chem.* 60:7508–7510 (1995).

Ishiyama et al., "Synthesis of Arylboronates via the Palladium(0)–Catalyzed Carbonylative Cross–Coupling Reaction of Tetra(alkoxo)diborons with Aryl Triflates," *Tetra. Lett.* 34:3447–3450 (1997).

Ishiyama et al., "Synthesis of Unsymmetrical Biaryl Ketones via Palladium–Catalyzed Carboylative Cross–Coupling Reaction of Arylboronic Acids with Iodoarenes," *Tetra Lett.* 34:7595–7598 (1993).

IUPAC–IUB Commission on Biochemical Nomenclature. Abbreviations and symbols for the description of the conformation of polypeptide chains. *J. Mol. Biol.* 52:1–17 (1970).

Iwatsuka et al., "General Survey of Diabetic Features of Yellow KK Mice,"*Endocrinol. Japon.* 17:23–35 (1970).

Jain, "Scoring Non–Covalent Ligand–Protein Interactions: A Continuous Differential Function Tuned to Compute Binding Affinities," *J. Comp. Aided Mol. Des.* 10(5):427–440 (1996).

Jung et al., "New Efficient Method for the Total Synthesis of (S,S)–Isodityrosine from Natural Amino Acids," *J. Org. Chem.* 64:2976–2977 (1999).

Kamidawa et al., "Palladium–Catalyzed Amination of Aryl Bromides Utilizing Arene–Chromium Complexes as Ligands," *J. Org. Chem.* 63:8407–8410 (1998).

Kawai et al., "Enhance of Rat Urinary Bladder Tumorigenesis by Lipopolysaccharide–induced inflammation," *Cancer Res.* 53:5172–5175 (1993).

Krey et al., "Functional Interaction of Peroxisome Proliferator–Activated Receptor, Retinoid–X Receptor, and Sp1 in the Transcriptional Regulationof the Acyl–Coenzyme–A Oxidase Promoter," *Molecular Endocrinol.* 9:219–231 (1995).

Kriegler et al., "A Novel Form of TNF/Cachectin is a Cell Surface Cytotoxic Transmembrane Protein: Ramifications for the Complex Physiology of TNF," *Cell* 53:45–53 (1988).

Kyriakis et al., "Sounding the Alarm: Protein Kinase Cascades Activated by Stress and Inflammation," *J. Biol. Chem.* 271:24313–24316 (1996).

Lewis and Dean, "Automated site–directed drug design: the concept of spacer skeletons for primary structure generation," *Proc. R. Soc. Lond.* 236:125–162 (1989).

Littke et al., "A Convenient and General Method for Pd–Catalyzed Suzuki Croo–Couplings of Aryl Chlorides and Arylboronic Acids," *Angew. Chem. Int. Ed.* 37:3387–3388 (1998).

Mangelsdorf et al., "The Retinoid Receptors," *The Retinoids (Second Edition)* 319–349 (1994).

Manickam et al., "New Parts foe a Construction Set of Bifunctional Oligo(het)arylene Building Blocks foe Modular Chemistry," *Synthesis* 3:442–446 (2000).

McCann, "The Nitric Oxide Hypothesis of Brain Aging," *Exp. Gerontol.* 32:431–440 (1997).

McCann et al., "The Nitric Oxide Hypothesis of Aging," *Exp. Gerontol.* 33(7–8):813–826 (1998).

McKinlay and Rossman. Rational Design Antiviral Agents. *Annu. Rev. Pharmacol. Toxiciol.* 29:111–122 (1989).

Miyaura et al., "Palladium–Catalyzed Cross Coupling Reactions of Organoboron Ocmpounds," *Chem. Rev.* 95:2457–2483 (1995).

Molina et al., "The Role of Nitric Oxide in Neurodegeneration—Potential foe Pharmacological Intervention," *Drugs & Aging* 12(4):251–259 (1998).

Moroz et al., "The Ullmann Ether Condensation," *Russ Chem. Rev.* 43:679–689 (1974).

Moya–Camarena et al., "Conjugated linoleic acid is a potent naturally occuring ligand and activator of PPARα," *J. Lipid Res.* 40:1426–1433 (1999).

Mukherjee et al., "Sensitization of diabetic and obese mice to insulin by retiniod X receptor agonists," *Nature* 386:407–410 (1997).

Nestler et al., "A General Method for Molecular Tagging of Encoded Combinatorial Chemistry Libraries," *J. Org. Chem.* 59(17):4723–4724 (1994).

Dawson et al., "The Synthetic Chemistry of Retinoids," *Biology, Chemistry, and Medicine,* $2^{nd}$ Edition, Raven Press, Ltd., New York (1994).

Oliff, "The Role of Tumor Necrosis Factor (Cachectin) in Cachexia," *Cell* 54:141–142 (1988).

Paradisi, "Arene Substitution via Nucleophilic Addition to Electron Deficient Arenes," *Compreh. Org. Syn.* 4:423–450 (1991).

Perry and Davies, "Quantitative Structure–Activity Relationships in Drug Design," *QSAR* 189–193 (1989).

Petrov et al., "The Arbuzov Rearrangement with Participation of Halogenoacetylenes as a Method of Synthesis of Ethnylphosphonates and other Organo–phosphorus Compounds," *Russ. Chem. Rev.* 52:1030–1035 (1983).

Pohlman et al., "An Endothelial Cell Surface Factors(s) Induced in Vitro By Lipopolysaccharide, Interleukin 1, and Tumor Necrosis Factor–α Increases Adherence By a CDw18–Dependent Mechanism," *J. Immunol.* 136:4548–4553 (1986).

Pollock et al., "Purification and Characterization of Particulate Endothelium–derived Relaxing Factor Synthase from Cultured and Native Bovine Aortic Endothelial Cells,"*Proc. Natl. Acad. Sci.* 88:10480–10484 (1991).

Pujol–Borrell et al., "HLA Class II Induction in Human Islet Cells By Interferon–γ Plus Tumour Necrosis Factor kor Lymphotoxin," *Nature* 326:304–306 (1987).

Ripka, "Computers picture the perfect drug," *New Scientist* 54–57 (1988).

Rosin et al., "Inflammation, Chromosomal Instability, and Cancer: The Schistosomiasis Model,", *Cancer Res.* 54(Suppl, 7):1929s–1933s (1994).

Rouvinen et al., "Computer–Aided Drug Design," *Acta Pharmaceutica Fennica* 97 159–166 (1988).

Sanders, "Asthma, Viruses and Nitric Oxide," *Proc. Soc. Exp. Biol. Med.* 220(3):123–132 (1999).

Schandendorf et al., "Retinoic Acid Receptor—Selective Retiniods Exert Antiproliferative Effects on Human Melanoma Cell Growth In Vitro,"*Int. J. Oncol.* 5:1325–1331 (1994).

Schulman et al., "Transactivation by Retiniod X Receptor–Peroxisome Proliferator–Activated Receptor γ (PPARγa0 aaheterodimers: Intermolecular Synergy Requires Only the PPARγ Hormone–Dependent Activation Function," *Mol. Cell Biol.* 18:3483–3494 (1998).

Shao et al., "p53 Independent $G_0/G_1$ Arrest and Apoptosis Induced by a Novel Retinoid in Human Breast Cancer Cells," *Oncogene* 11:493–504 (1995).

Smith et al., "The Active Form of Tumor Necrosis Factor Is A Trimer," *J. Biol. Chem.* 262:6951–6954 (1987).

Spruce et al., "Heteroarotiniods. Synthesis, Characterization, and Biological Activity in Terms of an Assessment of these Systems to Inhibit the Induction of Orthine Decarboxylase Activity and to Induce Terminal Differtiation of HL–60 Cells," *J. Med. Chem.* 30–1474–1482 (1987).

Stanforth, "Catalytic Cross–Coupling Reactions in Biaryl Synthesis," *Tetrahedron* 54:263–303 (1998).

Stirling et al., "Increase In Exhale Nitric Oxide Levels in patients With Difficult Asthma and Correlation With Symptoms and Disease Severity Despite Treatment With Oral and Inhaled Corticosteriods," *Thorax* 53(12):1030–1034 (1998).

Strieter et al., "Endothelial Cell Gene Expression of a Neutrophil Chemotactic by TNF–α, LPS, and IL–1β," *Science* 243:1467–1469 (1989).

Suzuki, "New Synthetic Transformations Via Organoboron Compounds," *Pure & Applied Chem.* 66:213–222 (1994).

Teboul et al., "Thiazolidinediones and Fatty Acids Convert Myogenic Cells Into Adipose–like Cells," *J. Biol. Chem.* 270:21183–28187 (1995).

Thorns et al., "nNOS Expressing Neurons in the Entorhinal Cortex and Hippocampus Are Affected in Patients With Alzheimer's Disease," *Exp. Neurol.* 150:14–20 (1998).

Tietze et al., "The Knoevenagel Reaction," *Compreh. Org. Syn.* 2:341–394 (1991).

Tracey et al., "Tumor Necrosis Factor: A Pleiotropic Cytokine and Therapeutic Target," *Ann. Rev. Med.* 45:491–503 (1994).

Tracey et al., "Anti–Cachectin/TNF Monoclonal Antibodies Prevent Septic Shock During Lethal Bacteraemia," *Nature* 330:662–664 (1987).

Uysal et al., "Protection From Obesity–induced Insulin Resistance in Mice Lacking TNF–α Function," *Nature* 389:610–614 (1997).

Wadsworth, "Synthetic Application of Phosphoryl–Stabilized Anions," *Org. Reactions* 25:73–253 (1977).

Watanabe et al., "Synthesis of Sterically Hindered Biaryls via the Palladium–Catalyzed Cross–Coupling Reaction of Arylboronic Acids of Their Esters With Haloarenes," *Synlett.* 207–210 (1992).

Website: PDB database (http://www.pdb.org).

Welch et al., "Hammerhead: Fast, Fully Automated Docking of Flexible Ligands to Protein Binding Sites," *Chemistry and Biology* 3:449–462 (1996).

Wieberth et al., "Copper(I)–Activated Addition of Grignard Reagents to Nitriles. Synthesis of Ketimines, Ketones, and Amines," *J. Org. Chem.* 52:3901–3904 (1987).

Wilson et al., "The Structure–Activity Relationship Between Preoxisome Proliferator–Activated Receptor γ Agonism and the Antihyperglycemic Activity of Thiazolidinediones," *J. Med. Chem.* 39:665–668 (1996).

Wolfe et al., "Simple, Efficient Catayst System for the Palladium–Catalyzed Amination of Aryl Chlorides, Bromides, and Triflates," *J. Org. Chem.* 65:1158–1174 (2000).

Wolfe et al., "Scope and Limitations of the Pd/BINAP–Catalyzed Amination of Aryl Bromides," *J. Org. Chem.* 65:1144–1157 (2000).

Yi et al., "Gadd45 Family Proteins Are Coactivators of Nuclear Hormone Receptors," *Biochem. Biophys. Res. Commun.* 272:193–198 (2000).

Yun et al., "Neurobiology of Nitric Oxide," *Crit. Rev. Neurobiol.* 10:291–316 (1996).

Zask et al., "Synthesis of 3–Mercapto–2(5H)–Furanones via Reaction of Dilithio–2,4–thiazolidinedione Wiht α–Halo Ketones," *Tetra. Lett.* 34(17):2719–2722 (1993).

Zhang et al., "Negative Regulation of Peroxisome Proliferator–Activated Receptor–γ Gene Expression Contributes to the Antiadipogenic Effects of Tumor Necrosis Factor–α," *Mol. Endo.* 10:1457–1456 (1996).

Blondet et al., "Convenient Synthesis of 6–Methyl, 8–Methyl and 6,8–Dimethyl Derivatives of 5–Hydroxy–1, 2,3,4–Tetrahydro–2–Quinolinone," *Organic Preparation and Procedures Int.*, 25(2):223–228 (1993).

Cantello et al., "A Versatile Route to 2–Arylmethyl–1, 2–oxadiazolidine–3,5–diones via Regiospecific Alkyl–ation of 1,2,4–Oxadiazolidine–3,5–dione," *Synlett*, 263–264 (1997).

Cantello et al., "The Synthesis of BRL 49653—A Novel and Potent Antihyperglycaemic Agent," *Bioorganic & Medicinal Chemistry Letters*, 4:1181–1184 (1994).

Chang et al., "The Upjohn Colonoy of Kka$^y$Mice: A Model for Obese Type II Diabetes," *Elsevier Science Publishers B.V., Biomedical Division, Diabetes*, pp. 466–470 (1986).

Coleman "Diabetes–Obesity Syndromes in Mice," *Diabetes*, 31(1);1–6 (Apr. 1982).

Dawson et al., "Conformation Effects on Retinoid Receptor Selectivity. 2. Effects of Retinoid Bridging Group on Retinoid X Receptor Activity and Selectivity," *J. Med. Chemistry*, 38:3368–3383 (1995).

Gown, et al., "Human Atherosclerosis—II. Immunocytochemical Analysis of the Cellular Composition of Human Atherosclerotic Lesions," *Am. J. Pathol.*, 125(1):191–207 (1986).

Gray et al., "Practical Methylation of Aryl Halides by Suzuki–Miyaura Coupling," *Tetrahedron Letters*, 41:6237–6240 (2000).

Louie et al., "Palladium–Catalyzed Amination of Aryl Triflates and Importance of Triflate Addition Rate," *J. Org. Chem.*, 62:1268–1273 (1997).

Oram, "Molecular Basic of Cholesterol Homeostasis: Lessons from Tangier Disease and ABCA1," *Trends in Molecular Medicines*, 8(4):168–173 (2002).

Ross "Atherosclerosis—An Inflammatory Disease," *New England Journal of Medicine*, 340(2):115–126 (Jan. 1999).

Rust et al. "Tangier disease is caused by mutations in the gene encoding ATP–binding cassette transporter 1", *Nature Genetics*, 22:352–355 (Aug. 1999).

Serfaty–Lacrosniere et al., "Homozygous Tangier disease and cardiovascular disease," *Atherosclerosis*, 107:85–98 (1994).

Sparrow et al., "A Potent Synthetic LXR Agonist is More Effective than Cholesterol Loading at Inducing ABCA1 mRNA and Stimulating Cholesterol Efflux," *Journal of Biological Chemistry*, 277(12):10021–10027 (2002).

Thompson et al., "Effect of carcinogen dose and age at administration on induction of mammary carcinogenesis by 1–methyl–1–nitrosourea,"*Carginogenesis*, 13(9):1535–1539 (1992).

Walter et al., "The High Density Lipoprotein—and Apolipoprotein A–1–Induced Mobilization of Cellular Cholesterol is Impaired in Fibroblasts from Tangier Disease Subjects," *Biochemical and Biophysical Research Communications*, 205(1):850–856 (1994).

Zask et al., "Synthesis and Antihyperglycemic Activity of Novel 5–(naphthalenylsufonyl)–2,4–thiazolidinediones," *J.Med.Chem.*, 33:1418–1423 (1990).

Barclay et al., "ortho–Diquaternary aromatic compounds. III. Synthesis and reactions of polyslkyltetralones and derivatives," *Canadian Journal of Chemistry*, 48(17):2763–2775 (1970).

Bozdag, et al., "Synthesis and hypoglycemic activity of some new flavone derivatives 3$^{rd}$ Communication: 3'–flavonyl–2–4–thiazolidinediones," *Arzneimittel–Forschung* 50(7):626–630 (2000).

Bozdag, et al., "Synthesis and hypoglycemic activity of some new flavone derivatives 2$^{rd}$ Communication 4'–flavonyl–2–4–thiazolidinediones," *Arzneimittel–Forschung*, 50(6):539–543 (2000).

Cacchi et al., "Palladium–Catalyzed Triethylammounium Formate Reduction of Aryl Triflates. A Selective Method for the deoxygenation of phenols," *Tetrahedron Letters*, 27(45):5541–5544 (1986).

Dawson et al., "The Synthetic Chemistry of Retinoids," *Biology, Chemistry, and Medicine*, 2$^{nd}$ Edition, Raven Press, Ltd., New York (1994).

Ertan et al., "Synthesis and antihyperglycemic activity of novel flavonyl 2, 4–thiazolidinediones," *Acta Pharmaceutica Turcica*, 39(1):33–37 (1997).

Faul et al., "Synthesis of Novel Retinoid X Receptor–Selective Retinoids," *J. Org. Chem.*, 66:5572–5782 (2001).

Xiong et al., "Human D–Type Cyclin," *Cell*, 65:691–699 (1991).

RXR ACTIVATING MOLECULES

I. CROSS REFERENCE TO RELATED APPLICATIONS

This application claims priority to U.S. provisional application No. 60/274342, for RXR Activating Molecules, filed on Mar. 8, 2001, which is herein incorporated by reference in its entirety. U.S. Ser. No. 09/652,810, and U.S. Ser. No. 09/655,460, both filed Aug. 31, 2000, are also hereby incorporated by this reference in their entireties.

II. BACKGROUND OF THE INVENTION

Type 2 diabetes, also referred to as non-insulin dependent diabetes mellitus (NIDDM), is the major cause of diabetes in developed countries. In the United States alone, approximately 17 million people, and more than 120 million worldwide, are affected. Because this disorder is a late onset disease and occurs often in overweight persons, it can be expected that the number of patients suffering from this disease will increase further. Patients suffering from type 2 diabetes usually still produce insulin, but become increasingly resistant to their own insulin and insulin therapy. A promising new class of drugs has been recently introduced that resensitizes patients to their own insulin (insulin sensitizers), thereby reducing blood glucose and triglyceride levels, and thus abolishing, or at least reducing, the requirement for exogenous insulin. Rosiglitazone (Avandia™) and Pioglitazone (Actos™) bind to the nuclear receptor PPARγ and are the first representatives of this class of receptor ligands approved for the treatment of type 2 diabetes in the United States and several other countries. These compounds, however, have side effects including rare but severe liver toxicities (i.e., troglitazone) and they can increase body weight and cause edema in humans and may also lead to a worsening situation for. patients with certain heart conditions. Such side effects are of major concern for patients who might require treatment for a decade or longer. Therefore, new and better drugs for the treatment of type 2 diabetes and related disorders are needed. Ligands for the retinoid X receptor (RXR) have been suggested and examined as alternative choices for the development of a new class of insulin sensitizer drugs, that could avoid side effects seen with the PPARγ insulin sensitizers. RXR ligands can also influence cholesterol metabolism and transport and could therefore address additional aspects such as hypercholesteremia and arteriosclerosis, often seen with type 2 diabetic patients. In fact, a majority of type 2 diabetic patients appear to die of an arteriogenic event. However, typical RXR ligands lead to increases in triglyceride levels in animals and humans, which makes them undesirable for the treatment of most type 2 diabetic patients that very often have already elevated blood triglyceride levels. A subgroup of heterocyclic derivatives that does not lead to such undesirable side effects and which interacts with RXR in a highly specific manner is disclosed. Such RXR ligands with these unexpected properties are useful for the treatment of type 2 diabetes, hypercholesteremia, arteriosclerosis and disorders related to these diseases. Disclosed are molecules that interact with a side pocket of their specific receptor ligand-binding domain, where the receptor is a retinoid X receptor. Such molecules are useful for the treatment of type 2 diabetes, hypercholesteremia and related diseases, including arteriosclerosis.

III. SUMMARY OF THE INVENTION

In accordance with the purpose(s) of this invention, as embodied and broadly described herein, this invention, in one aspect, relates to a molecule that activates an RXR receptor, wherein the molecule comprises an RXR binding portion which binds the RXR receptor and comprises a side pocket contacting residue which contacts a side-pocket 1 of an RXR receptor.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

IV. BRIEF DESCRIPTION OF THE DRAWINGS

The accompanying drawings, which are incorporated in and constitute a part of this specification, illustrate several exemplary embodiments of the invention and together with the description serve to explain the principles of the invention.

FIG. 1 shows the Connolly surface of the entire active site of RXR, with one amino acid Arg A316 shown for reference. The Connolly surface is generated as described in IUPAC-IUB Commission on Biochemical Nomenclature (1970). Abbreviations and symbols for the description of the conformation of polypeptide chains. J. Mol. Biol., 52, 1–17.

Figure 3:
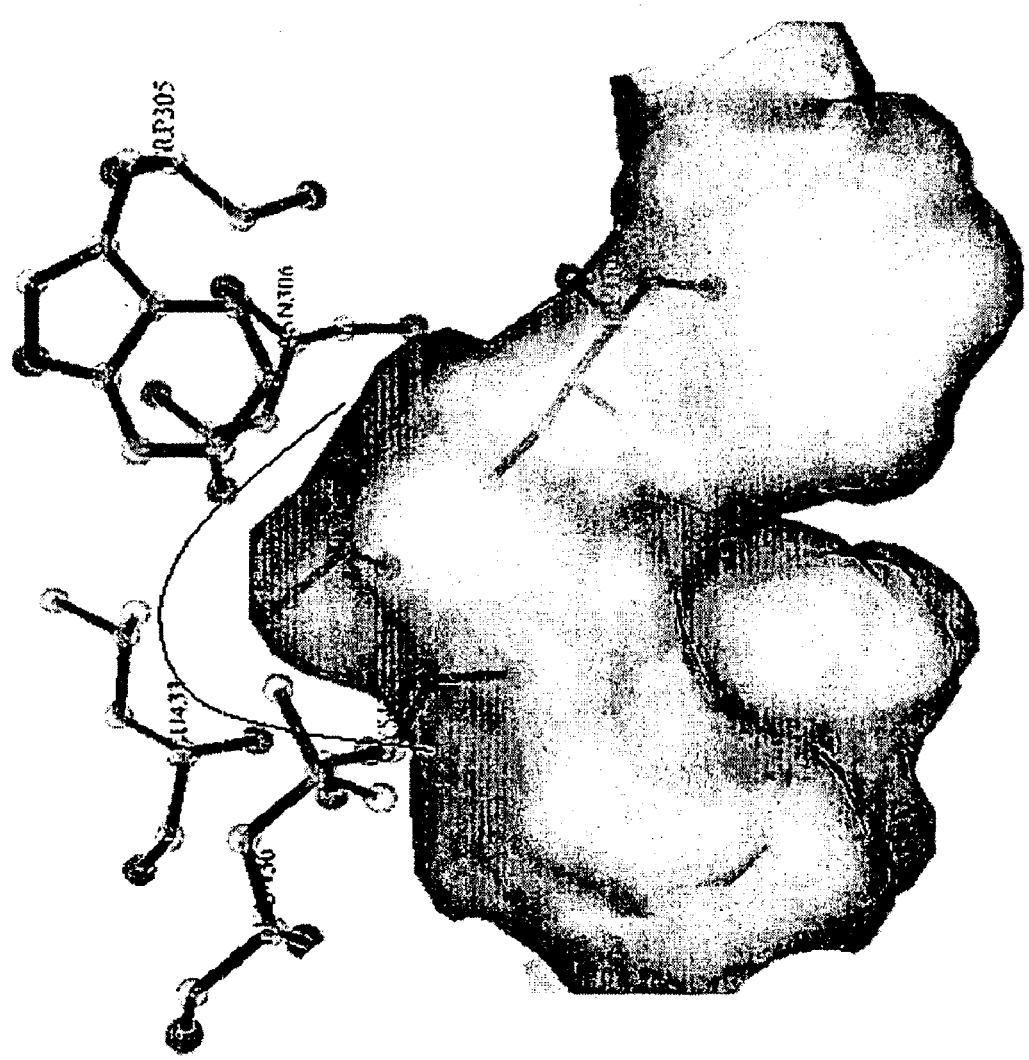
FIG. 3 shows the amino acids lining side pocket 1.
Figure 5:
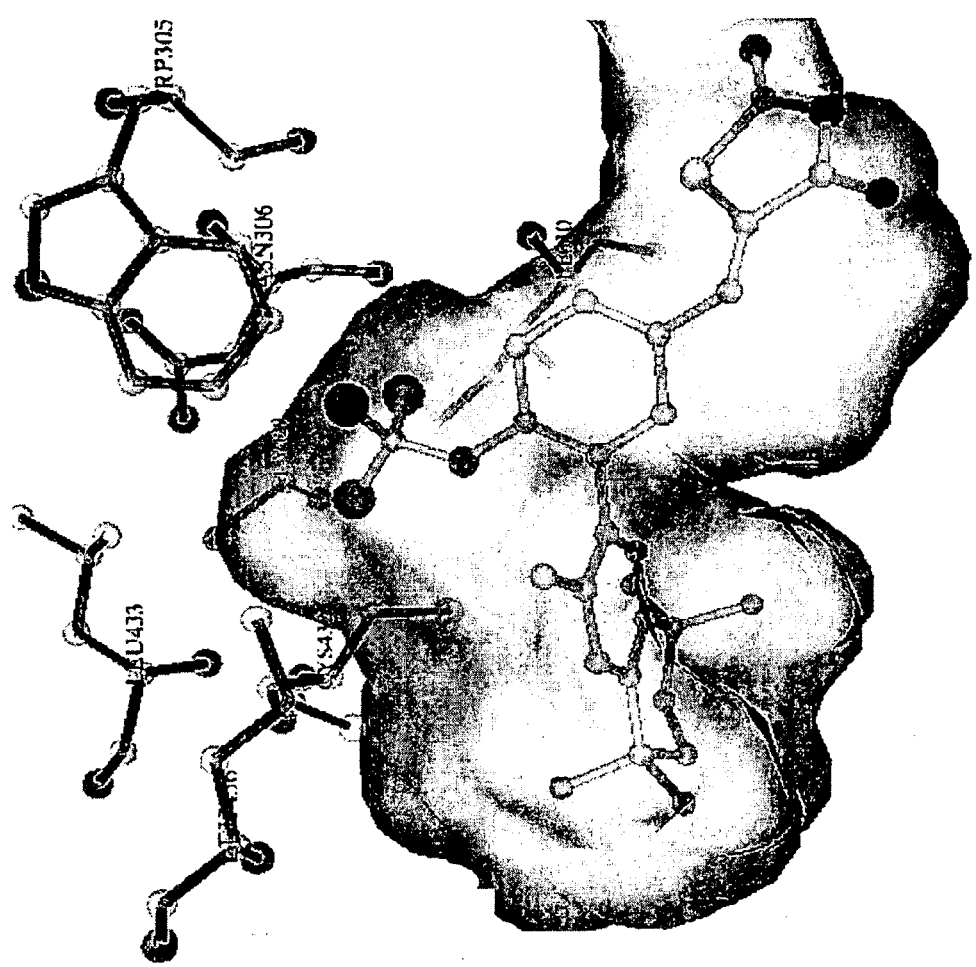

FIG. 5 shows the same view of FIG. 3 with compound 1 in the RXR ligand pocket. Note that compound 1 has a side pocket 1 contacting residue.

Figure 6:
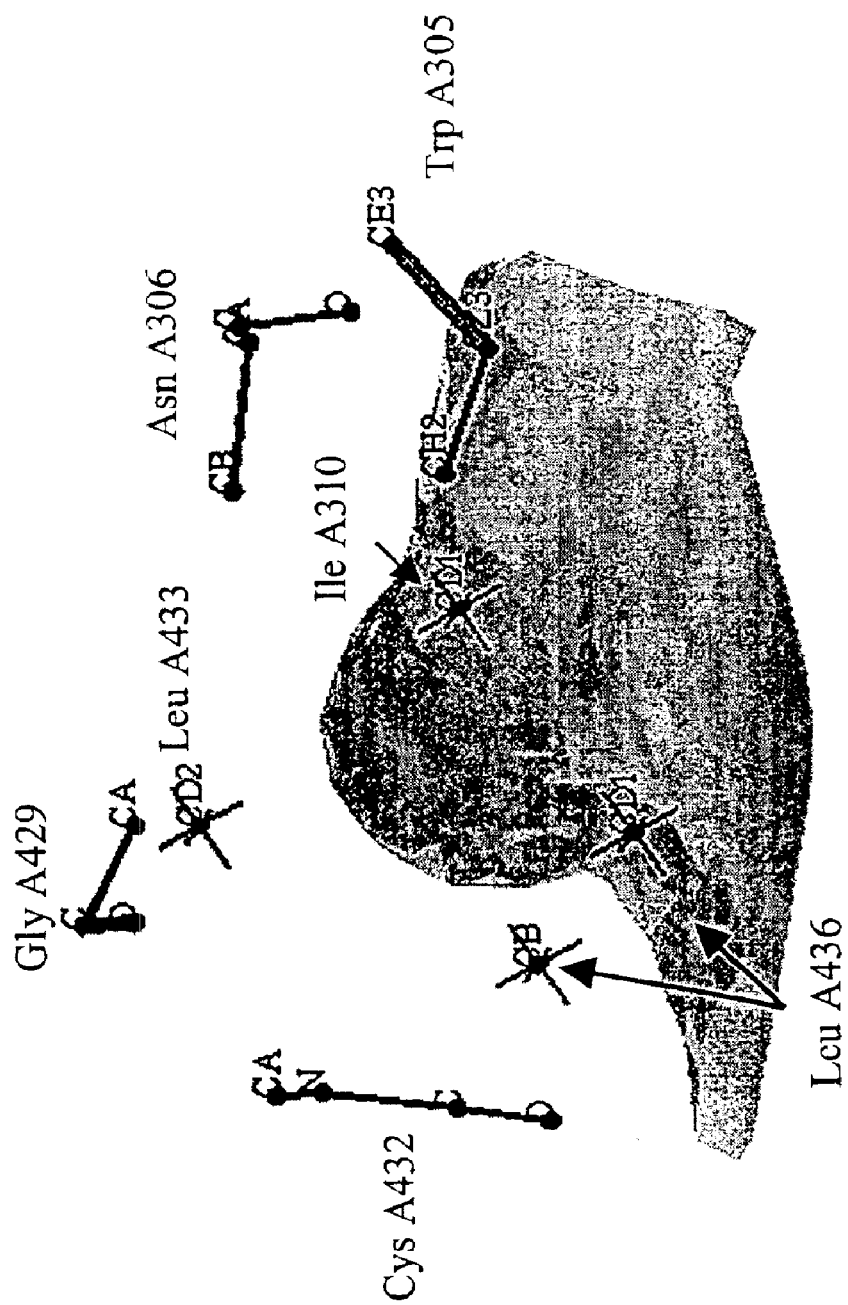

FIG. 6 shows the labeling of specific atoms from the amino acids shown in FIG. 3 that are close to the Connolly surface of the side pocket 1. In this figure, wherever connected atoms are selected, they are shown as lines connecting the atoms. Wherever isolated atoms are selected, stars represent these atoms. Where Association of the name and the atom requires, an arrow is provided pointing from the amino acid name to the individual atoms (as in, for example, Leu A436). The list of specific atoms are those of C1L.

Figure 7:
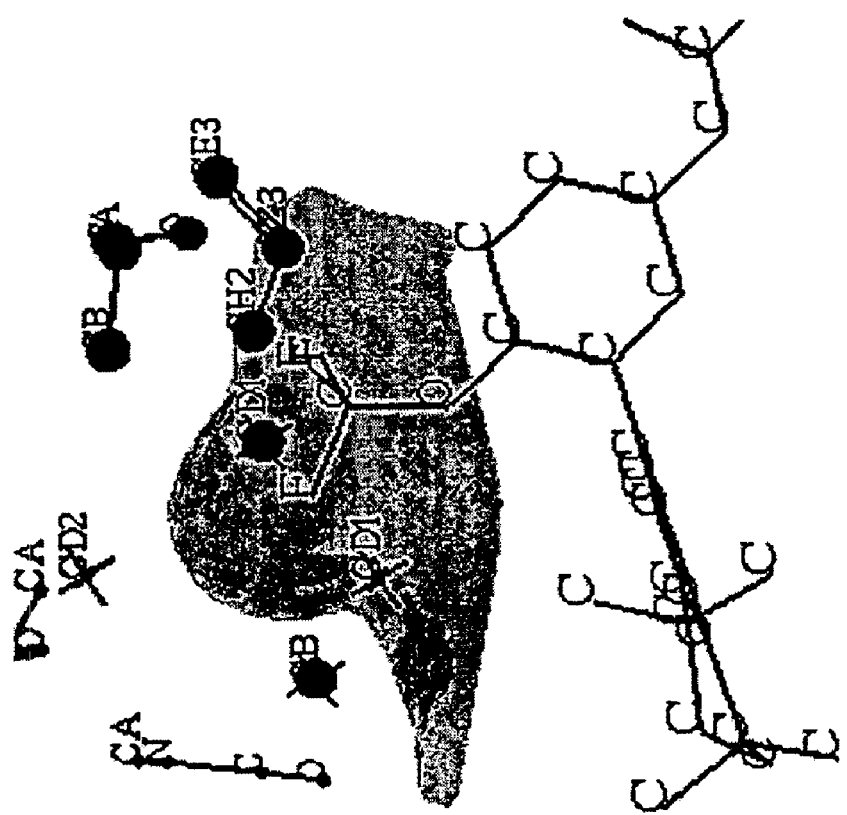

FIG. 7 shows the position of compound 1 relative to the Connolly surface of the side pocket 1. Note that compound 1 has a side pocket 1 contacting residue.

Figure 8:
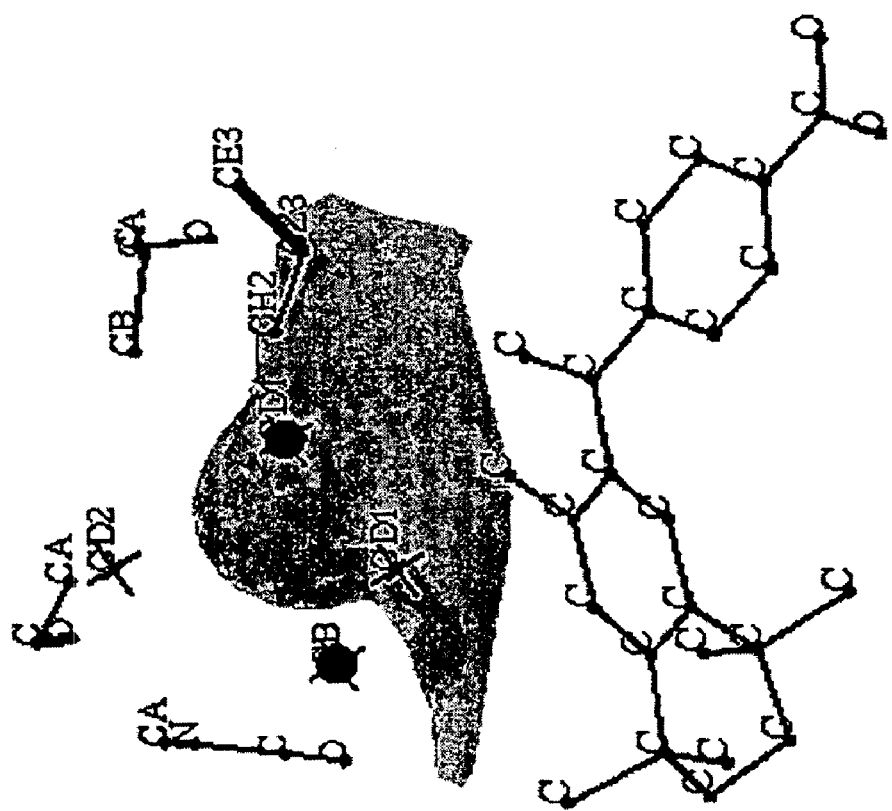

FIG. 8 shows the position of compound 2 relative to the Connolly surface of the side pocket 1.

Figure 9:
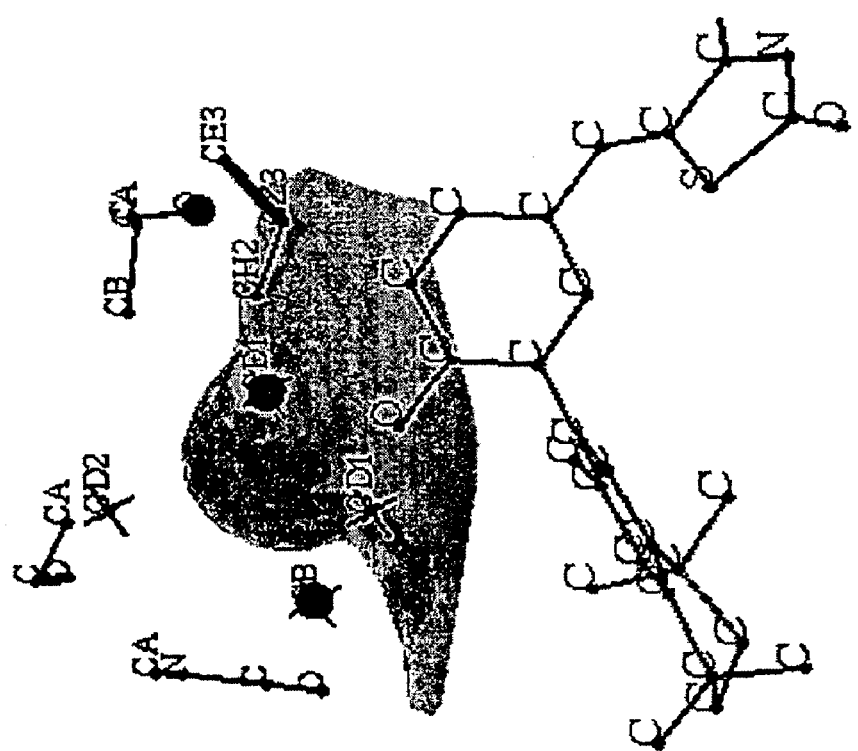

FIG. 9 shows the position of compound 4 relative to the Connolly surface of the side pocket 1.

Figure 10:
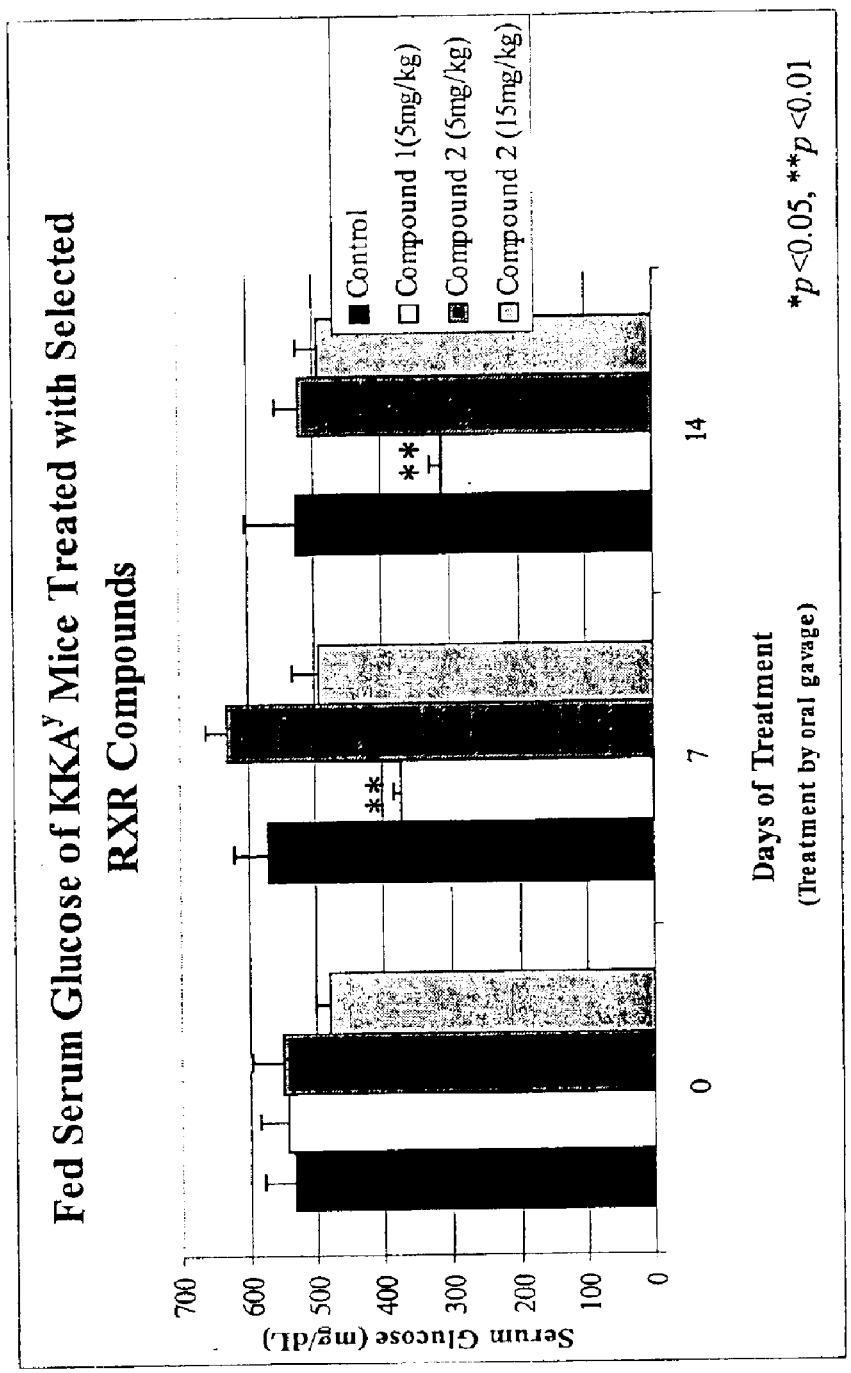

FIG. 10 shows adult diabetic $KKA^y$ mice were housed in a fixed 12—12-hr artificial light-dark cycle, and maintained on a standard rodent diet. Prior to commencing treatment, all of the animals are bled from the tail vein and serum levels of glucose and triglyceride are measured in duplicate. The animals are then sorted into different treatment groups with equal average triglyceride levels. The animals are treated with a single daily oral dose of the test compound suspended in sesame oil (dose volume of 3 ml/kg). Type 2 diabetic KKA$^y$ mice treated with Compound 1 at 5 mg/kg showed a significant decrease in serum glucose levels compared to vehicle treated control mice (p≦0.01: Fisher's LSD test). By contrast, diabetic mice treated with Compound 2 at 5 and 15 mg/kg showed no difference in serum glucose levels compared to vehicle treated controls.

Figure 11:
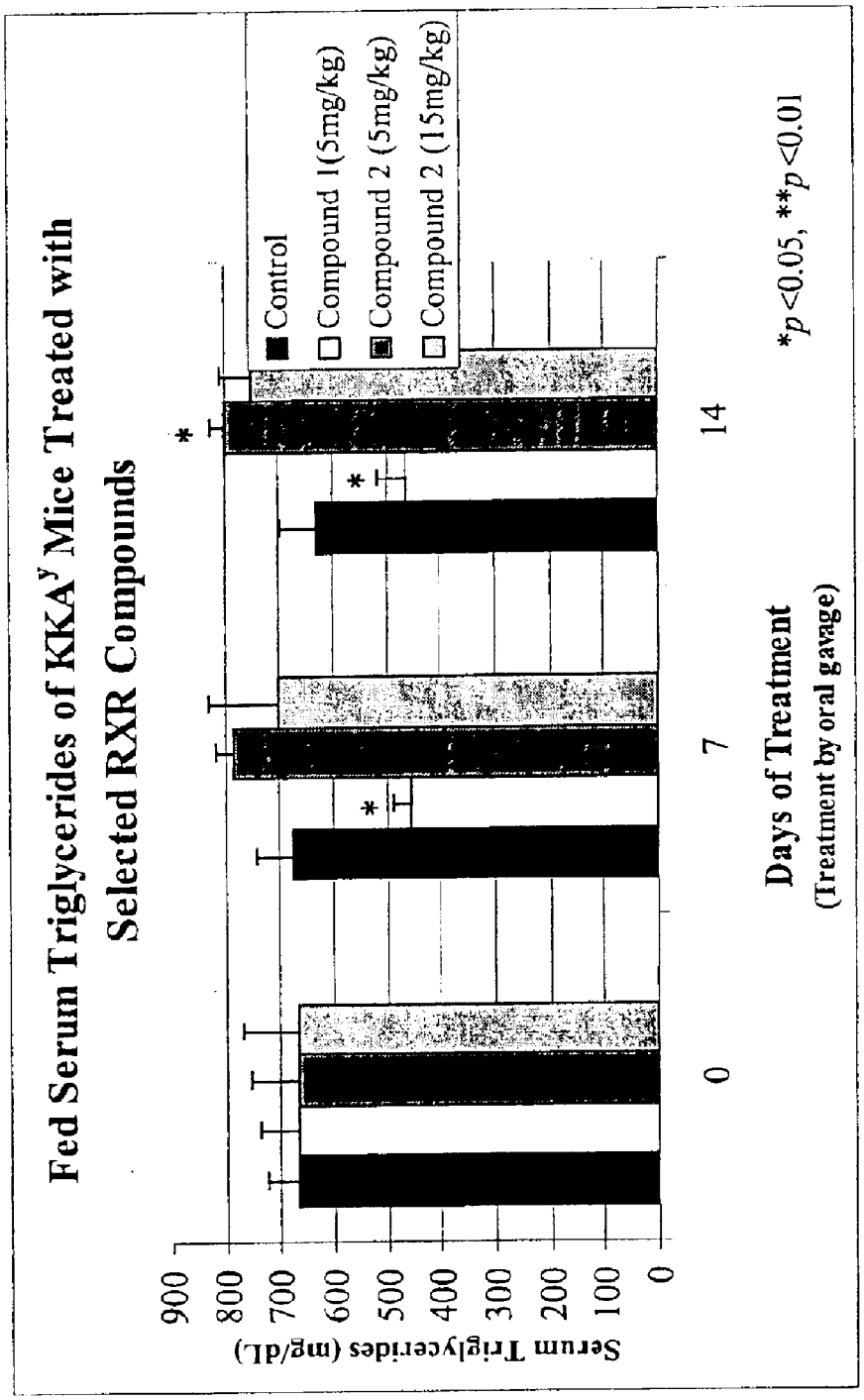

FIG. 11 shows type 2 diabetic KKA$^y$ mice were treated as described in FIG. 10 legend. Animals treated with Compound 1 at 5 mg/kg showed a significant decrease in serum triglyceride levels compared to vehicle treated control mice (p≦0.05; Fisher's LSD test). By contrast, diabetic mice treated with Compound 2 at 5 and 15 mg/kg showed an increase in serum triglyceride levels compared to vehicle treated controls (statistically significant at 5 mg/kg, p≦0.05; Fisher's LSD test).

Figure 12:
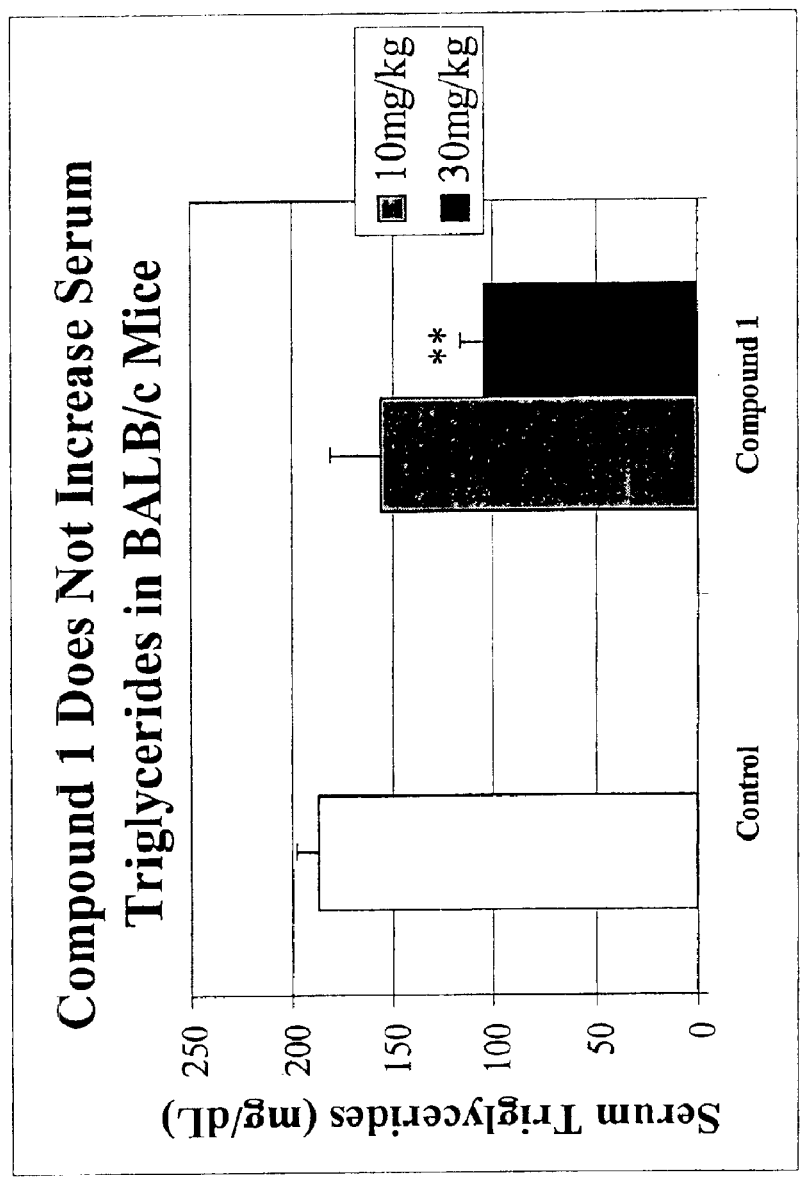

FIG. 12 shows adult male BALB/c mice were housed in a fixed 12—12-hr artificial light-dark cycle, and maintained on a standard rodent diet. The animals were treated with a single daily oral dose of the test compound suspended in sesame oil (dose volume of 5 ml/kg). Treatment was for 14 days, Animas treated with 10 and 30 mg/kg of Compound 1, which are doses that are 30 and 100 times the efficacious does in diabetic db/db mice, respectively, caused no increase in serum triglyceride levels compared to vehicle treated control animals.

Figure 13:
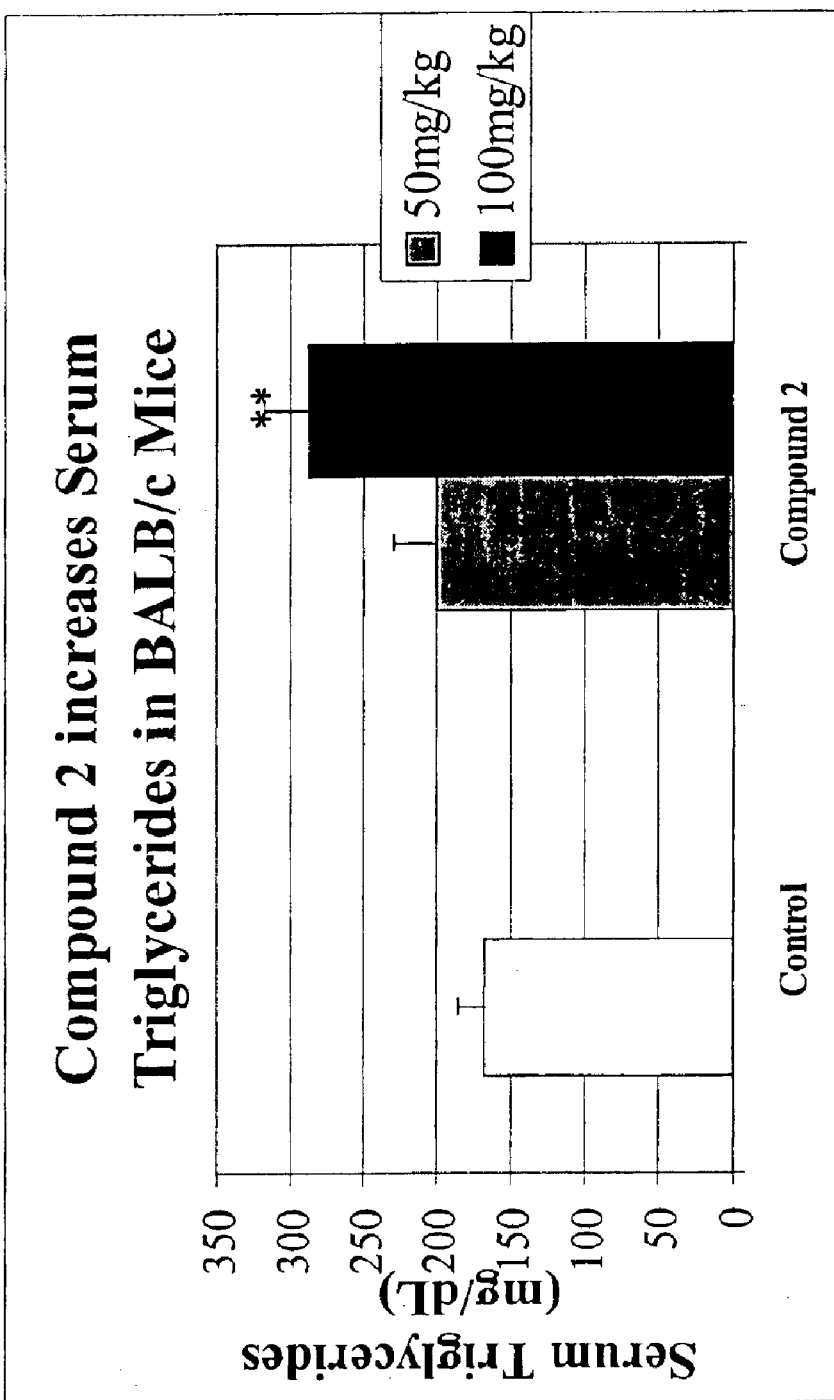

FIG. 13 shows adult BALB/c mice were treated as described in the FIG. 12 legend. Animals treated with 50 and 100 mg/kg of Compound 2 showed an increase in serum triglyceride levels compared to vehicle treated control animals (statistically significant at 100 mg/kg, p≦0.01; Fisher's LSD test).

Figure 14:
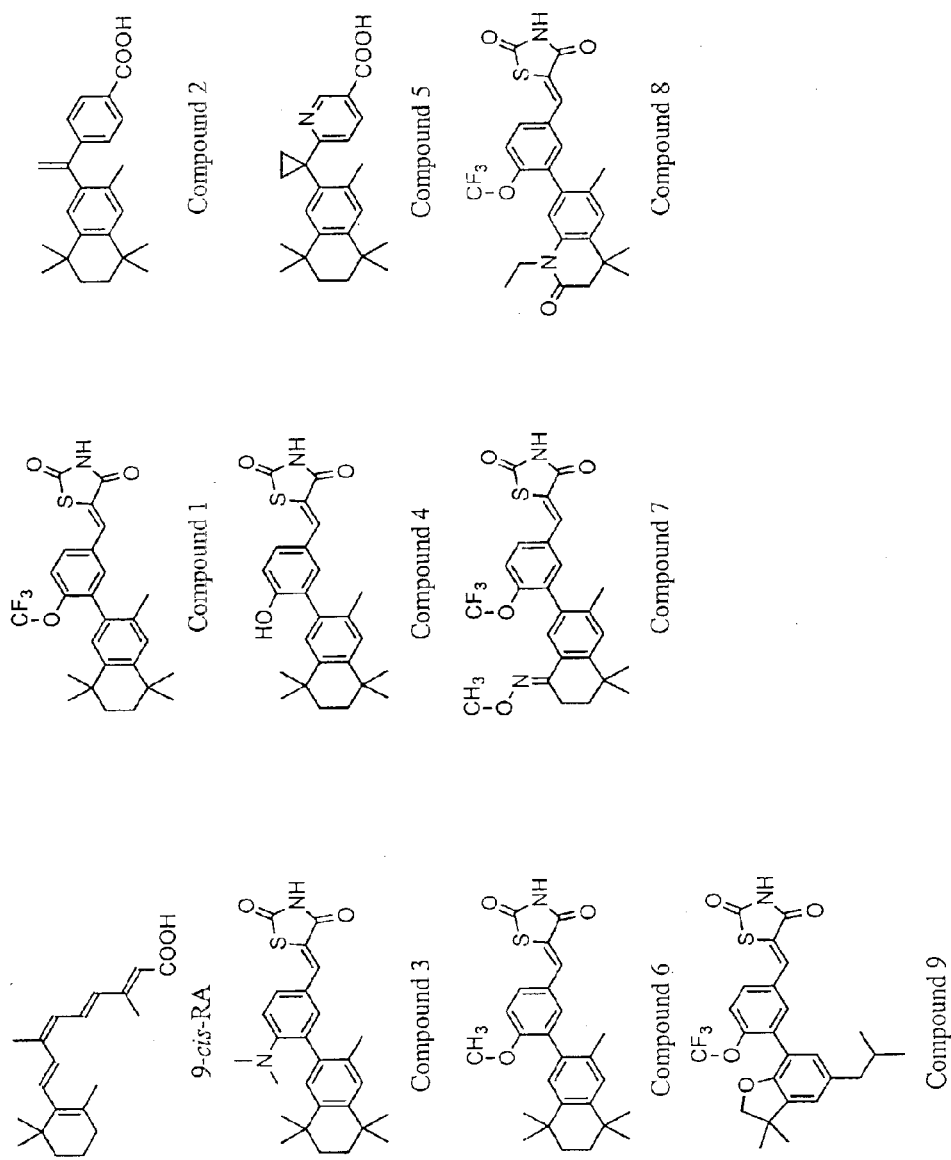

FIG. 14 shows chemical structures of various compounds.

Figure 15:
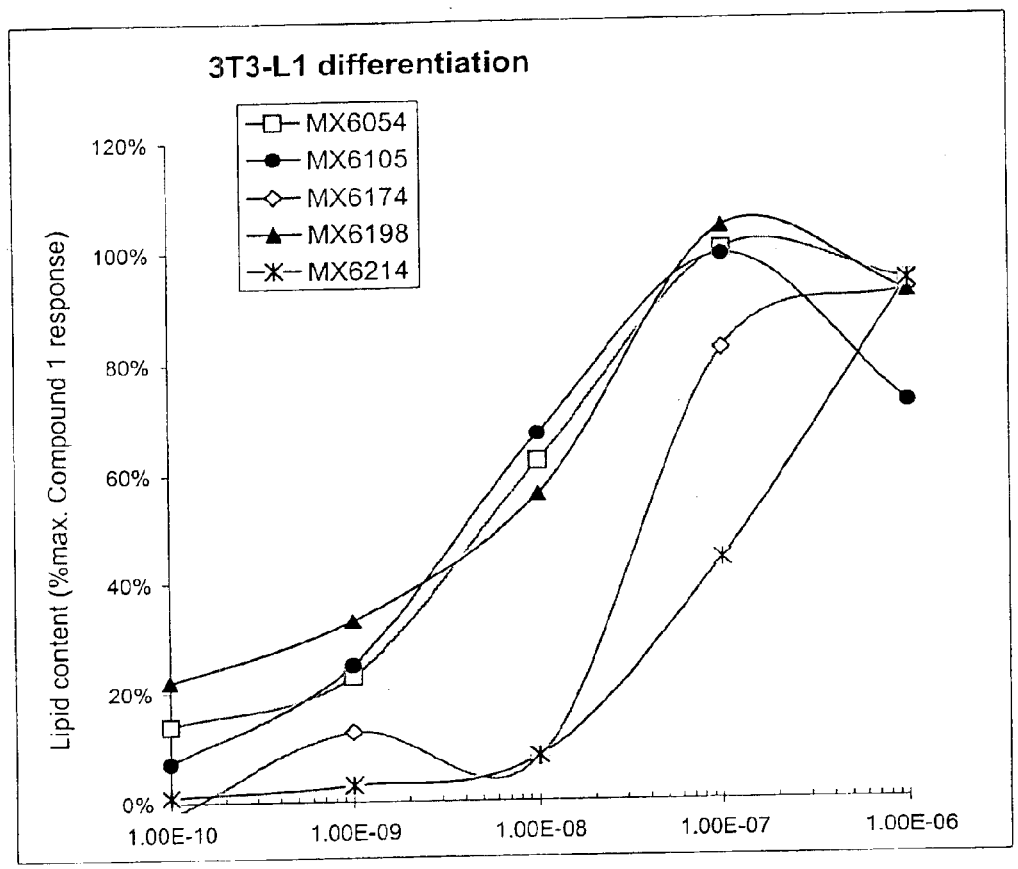

FIG. 15 shows a 3T3-L1 differentiation Assay. Mouse 3T3-L1 cells were grown in 96-well tissue culture plates containing growing medium (DME containing 10% calf serum (CS) plus glutamine-pen-strep) at a density of 3,000 cells/well. Two days after reaching confluence, cells are treated with the different compounds in DM (Day 0). Compound 1 is included in all the experiments, and its ability to differentiate 3T3-L1 cells at 0.1 µM is taken as reference for 100% differentiation. After 7 days the lipid content of the cells was determined.

Figure 16:
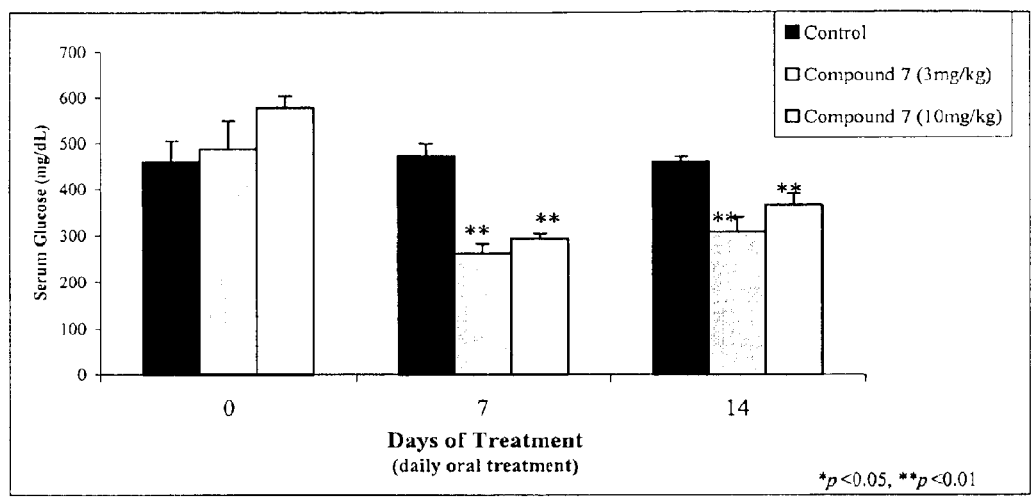

FIG. 16 shows glucose lowering activity for compound 7 as disclosed herein.

Figure 17:
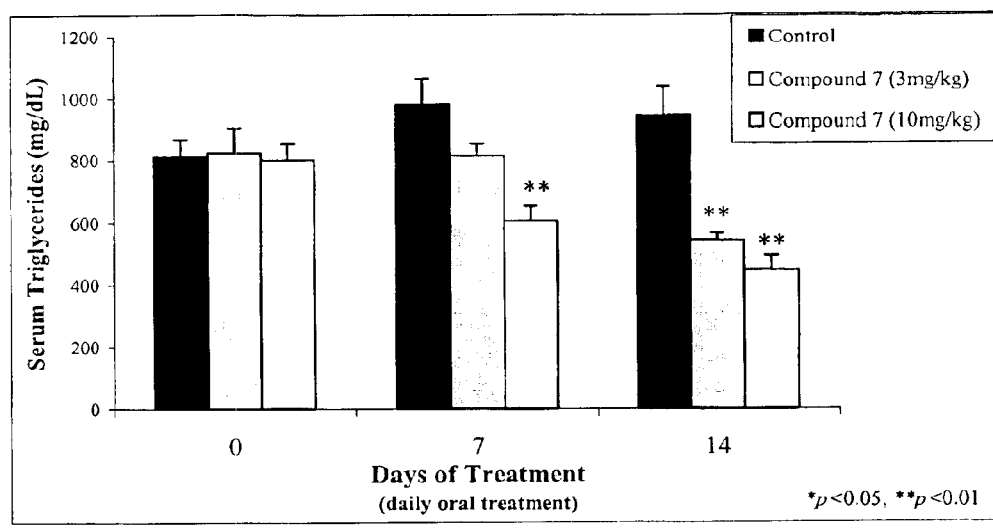

FIG. 17 shows triglyceride lowering activity for compound 7 as disclosed herein.

V. DETAILED DESCRIPTION

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods or to specific reagents, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

In the specification and Formulae described herein the following terms are hereby defined.

The term "alkyl" denotes a radical containing 1 to 12 carbons, such as methyl, ethyl, n-propyl, iso-propyl, n-butyl, sec-butyl, t-butyl, amyl, t-amyl, n-pentyl and the like.

The term "alkenyl" denotes a radical containing 1 to 12 carbons such as vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" denotes a radical containing 1 to 12 carbons, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "substituted alkyl" denotes a radical containing 1 to 12 carbons of the above definitions that are substituted with one or more groups, but preferably one, two or three groups, selected from hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, trihaloalkyl, alkoxy, substituted alkoxy or haloalkoxy. When more than one group is present then they may be the same or different.

The term "substituted alkenyl" denotes a radical containing 1 to 12 carbons of the above definitions that are substituted with one or more groups, but preferably one, two or three groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they may be the same or different.

The term "substituted alkynyl" denotes a radical containing 1 to 8 carbons of the above definitions that are substituted with one or more groups, but preferably one or two groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy.

The term "cycloalkyl" denotes a radical containing 3 to 8 carbons, such as cyclopropyl, cyclobutyl, (cyclopentyl, cyclopenyl, cyclohexyl, cycloheptyl and the like. The term "substituted cycloalkyl" denotes a cycloalkyl as defined above that is further substituted with one or more groups selected from halogen, alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is, substituted with more than one group, they may be the same or different.

The term "cycloalkenyl" denotes a radical containing 3 to 8 carbons, such as cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like. The term "substituted cycloalkenyl" denotes a cycloalkyl as defined above further substituted with one or more groups selected from halogen, alkyl, hydroxyl, alkoxy, substituted alkoxy, haloalkoxy, carboxy, carboalkoxy., alkylcarboxamide, substituted alkylcarboxamide, dialkylcarboxamide, substituted dialkylcarboxamide, amino, mono-substituted amino or di-substituted amino. When the cycloalkenyl is substituted with more than one group, they may be the same or different.

The term "alkoxy" as used herein denotes a radical alkyl, defined above, attached directly to an oxygen such as methoxy, ethoxy, n-propoxy, iso-propoxy, n-butoxy, t-butoxy, iso-butoxy and the like.

The term "substituted alkoxy" denotes a radical alkoxy of the above definition that is substituted with one or more groups, but preferably one or two groups, selected from hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they may be the same or different.

The term "mono-substituted amino" denotes an amino substituted with one group selected from alkyl, substituted alkyl or arylalkyl wherein the terms have the same definitions found throughout.

The term "di-substituted amino" denotes an amino substituted with two radicals that may be same or different selected from aryl, substituted aryl, alkyl, substituted alkyl or arylalkyl wherein the terms have the same definitions found throughout. Some examples include dimethylamino, methylethylamino, diethylamino and the like.

The term "haloalkyl" denotes a radical alkyl, defined above, substituted with one or more halogens, preferably fluorine, such as a trifluoromethyl, pentafluoroethyl and the like.

The term "haloalkoxy" denotes a haloalkyl, as defined above, that is directly attached to an oxygen to form trifluoromethoxy, pentafluoroethoxy and the like.

The term "acyl" denotes a radical containing 1 to 8 carbons such as formyl, acetyl, propionyl, butanoyl, iso-butanoyl, pentanoyl, hexanoyl, heptanoyl, benzoyl and the like.

The term "acyloxy" denotes a radical containing 1 to 8 carbons of an acyl group defined above directly attached to an oxygen such as acetyloxy, propionyloxy, butanoyloxy, iso-butanoyloxy, benzoyloxy and the like.

The term "aryl" denotes an aromatic ring radical containing 6 to 10 carbons that includes phenyl and naphthyl. The term "substituted aryl" denotes an aromatic radical as defined above that is substituted with one or more selected from hydroxyl, cycloalkyl, aryl, substituted aryl, heteroaryl, heterocyclic ring, substituted heterocyclic ring, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, alkylthio, alkoxy, substituted alkoxy or haloalkoxy, wherein the terms are defined herein, The term "halo" or "halogen" refers to a fluoro, chloro, bromo or iodo group.

The term "thioalkyl" denotes a sulfide radical containing 1 to 8 carbons, linear or branched. Examples include methylsulfide, ethyl sulfide, isopropylsulfide and the like.

The term "thiohaloalkyl" denotes a thioalkyl radical substituted with one or more halogens. Examples include trifluoromethylthio, 1,1-difluoroethylthio, 2,2,2-trifluoroethylthio and the like.

The term "carboalkoxy" refers to an alkyl ester of a carboxylic acid, wherein alkyl has the same definition as found above. Examples include carbomethoxy, carboethoxy, carboisopropoxy and the like.

The term "alkylcarboxamide" denotes a single alkyl group attached to the amine of an amide, wherein alkyl has the same definition as found above. Examples include N-methylcarboxamide, N-ethylcarboxamide, N-(iso-propyl)carboxamide and the like. The term "substituted alkylcarboxamide" denotes a single "substituted alkyl" group, as defined above, attached to the amine of an amide.

The term "dialkylcarboxamide" denotes two alkyl or arylalkyl groups that are the same or different attached to the amine of an amide, wherein alkyl has the same definition as found above. Examples of a dialkylcarboxamide include N,N-dimethylcarboxamide, N-methyl-N-ethylcarboxamide and the like. The term "substituted dialkylcarboxamide" denotes two alkyl groups attached to the amine of an amide, where one or both groups is a "substituted alkyl", as defined above. It is understood that these groups may be the same or different. Examples include N,N-dibenzylcarboxamide, N-benzyl-N-methylcarboxamide and the like.

The term "alkylamide" denotes an acyl radical attached to an amine or monoalkylamine, wherein the term acyl has the same definition as found above. Examples of "alkylamide" include acetamido, propionamido and the like.

The term "arylalkyl" defines an alkylene, such as —$CH_2$— for example, which is substituted with an aryl group that may be substituted or unsubstituted as defined above. Examples of an "arylalkyl" include benzyl, phenethylene and the like.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— repeat units in the polyester, regardless of whether ethylene glycol is used to prepare the polyester.

Similarly, a 2,4-thiazolidinedione residue in a chemical compound refers to one or more -2,4-thiazolidinedione moieties of the compound, regardless of whether the residue was obtained by reacting 2,4-thiazolidinedione to obtain the compound.

The term the "RXR binding portion" as used herein refers a part of the molecules of the invention that is bound to but excludes the side pocket contacting residue. The RXR binding portion is an organic residue of a suitable polarity, size, and shape, so as to fit within and become bound to and/or complexed to the ligand binding domain of the RXR receptor that binds 9-cis retinoic acid as described by Egea et.al. The RXR binding portion is an organic residue that can serve various functions, which includes contributing at least a significant proportion of the interactions with the RXR receptor which bind the molecules, and additionally provides the function of supporting and geometrically directing the side pocket contacting residue so as to come into contact with side pocket 1.

The term "cyclic organic residue" as used herein refers to a sub-portion of the RXR binding portion, comprising a cyclic organic residue having one or more cyclic rings, and from 2 to 18 carbon atoms, or preferably from about 4 to 12 carbon atoms. The cyclic organic residue may contain suitable heteroatoms, which include but are not limited to nitrogen, oxygen, and sulfur, so as lo form heterocyclic organic residues, which are a well known class of compounds to those of skill in the art. The cyclic organic residue may be saturated, unsaturated, or aromatic, and is preferably aromatic. The cyclic organic residue is bonded to the side pocket contacting residue, and can serve various functions, which includes at least the function of supporting and geometrically directing the side pocket contacting residue so as to come into contact with side pocket 1. The cyclic organic residue may be unsubstituted, but preferably is substituted with one or more organic or inorganic substituent groups or residues, including but not limited to a halide, a hydroxide, a thiol, an amino, an alkyl, an aryl, a heteroaryl, an alkoxy, or other well known organic or inorganic groups or residues as defined in the definitions section of this application. Preferably, the cyclic organic residue is bonded to one or both of the polar organic binding portions, and/or the organic portion, as described herein below.

The term the "polar binding portion," as used herein refers to a sub-portion of the RXR binding portion that is optionally bound to the cyclic organic residue. The polar binding portion can serve various functions, which include contributing at least a significant proportion of the binding interactions with the RXR receptor, especially by interacting with the relatively polar portions of the RXR receptor (as described by Egea et.al.)that normally binds the carboxyl group of 9-cis retinoic acid.

The term the "organic binding portion," as used herein refers to a sub-portion of the RXR binding portion that is optionally bound to the cyclic organic residue. The polar organic binding portion can serve various functions, which include contributing at least a significant proportion of the binding interactions with the RXR receptor, especially by interacting with the relatively non-polar portions of the RXR receptor (as described by Egea et.al.) that normally binds the cyclohexenyl residue of 9-cis retinoic acid. Reference will now be made in detail to the present preferred embodiment(s) of the invention, an example(s) of which is [are] illustrated in the accompanying drawings. Wherever possible, the same reference numbers are used throughout the drawings to refer to the same or like parts.

A molecule can be considered to activate an RXR if the molecule shows 60% of the activity of the agonist 9-cis retenoic acid at $10^{-6}$ M which activity can be considered to activate transcription in the RXR transcription assay discussed in Example 4.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

A. Compositions

This invention provides a molecule that activates an RXR receptor, wherein the molecule comprises an RXR binding portion which binds the RXR receptor and comprises a side pocket contacting residue which contacts side-pocket 1 of an RXR receptor. The side pocket can comprise at least 4 or more contacts between the atoms of the side pocket.

1. RXR Receptors a) Retinoid X Receptors (RXR)

(1) Function

RXRs belong to the large family of nuclear receptor proteins. This family of receptors includes the estrogen, androgen, thyroid hormone (TR), vitamin D3 (VDR) and other receptors that can be activated by small molecule hormones, vitamins and other signal molecules as has been reviewed, for instance by Mangelsdorf D J, Umesono K, Evans R: *The Retinoid Receptors*. In: *The Retinoids (Second Edition)*, Spom M B, Roberts A B, Goodman D S (Eds.), Academic Press, Inc., Orlando, Fla. (1994):319–349. RXRs are part of the retinoid receptor subgroup which consists of two classes of receptors: the retinoic acid receptors (RARs) and the retinoid X receptors (RXRs). Each class contains three subtypes, α, β and γ (encoded by separate genes), of which various isoforms are expressed in a tissue and development specific pattern. The receptors bind to small DNA segments called response elements from which they direct transcription in the presence of a ligand. RXRs also forms heterodimers with other receptors, such as TR, VDR and the PPARs. Through their interactions with PPARγ, RXRs can influence metabolic pathways that can be affected in type 2 diabetes patients (see Krey, et al., 1995, *Molecular Endocrinol.* 9:219–231 and Schulman, et al, 1998, *Mol. Cell Biol.* 18:3483–3494 and Mukhedjee, et al. 1997, *Nature.* 386:407–410). However, experience has shown that not all ligands for RXRs activate the same biological responses.

(2) Different RXR Receptor Subtypes

In mammals, including humans, RXR receptors are usually encoded by 3 genes: RXRα, β and γ. While certain portions, especially those of the amino terminal end of the RXRs can differ, RXRα, β and γ are essentially identical in the amino acids that make up their ligand binding domain. This also includes the amino acids that encode side pocket 1 in human RXRα, β and γ. The sequences of human RXRα, β and γ are shown.

b) Side Pocket

As described in more detail in examples 1 and 2, the side pocket 1 of human RXRα comprises amino acids Leu 436, Leu 433, Cys 432, Gly 429, Ile 310, Asn 306, and Trp 305. As discussed by others, (see Egea, et al. 2000, *EMBO J.* 19: 2592–2601) the various binding pockets are conserved between RXR subtypes. Thus, this cluster of amino acids can fulfill essentially the same roles in human RXRβ and γ. The exact amino acid position corresponding to the RXRα, positions can readily be determined by comparing SEQ ID Nos.

One way of defining the side-pocket 1 is at the level of the amino acids that make up the side-pocket 1. In human RXR alpha, side-pocket 1 can preferably be formed by the positioning of amino acids Leu 436, Leu 433, Cys 432, Ile 310, Asn 306, Gly 429 and Trp 305 all of SEQ ID) NO: 1. These seven amino acid residues, 2 Leu, cys, Ile, Asn, Gly and Trp, are highly conserved in other isoforms of RXR, such as, for example, RXRβ and RXRγ, and as such, are within the scope of the invention. The sequences of RXRα, RXR β and RXR γ are shown in SEQ ID Nos: 1, 2, and 3.

Side pocket 1 can be defined using the protein coordinates of human RXRα protein that has been determined and which has been deposited under 1FBY in the Protein Databank as further described in Example 1. Specifically, that portion of the protein coordinates of 1FBY that form side pocket 1, those atoms in amino acids Leu 436, Cys 432, Leu 433, Ile 310, Asn 306, Gly 429 and Trp 305. Herein amino acids are specified using the three letter amino acid code to specify the amino acid type, while the sequence number (for example 305, 306 or 310) is as reported in the crystal structure 1FBY from the Protein Databank. The prefix A specifies that the A polypeptide chain from 1FBY from the Protein Databank. The prefix A specifies that the A polypeptide chain from 1FBY is used. From these coordinates a cavity list can be made of the atoms of the amino acids making up the side pocket as disclosed herein. For example, specific atoms lining the side pocket 1 can comprise a "Cavity 1 List" (C1L). C1L can consist of TRP A305:CE3,CZ3,CH2; ASN A306:CA,C,O,CB,CG,ND2; ILE A310:CG1,CD1; GLYA429:0,C,CA; and LEU A433:N,CA,C,CD2, where individual atom names are defined in 1FBY. The side pocket formed by these atoms is illustrated in the Figures, which shows the amino acids comprising the pocket as line drawings, as well as a Connolly surface in the side pocket 1 region of the active site.

TABLE 1

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | K |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |

TABLE 1-continued

Amino Acid Abbreviations

| Amino Acid | Abbreviations | |
|---|---|---|
| serine | Ser | S |
| threonine | Thr | T |
| tyrosine | Tyr | Y |
| tryptophan | Trp | W |
| valine | Val | V |

2. Processed Molecules That Interact With RXR Receptors

The compositions that interact with the RXR receptors are typically processed molecules. Processed molecules are not naturally occurring molecules. For example, a molecule produced by synthetic methods would be a processed molecule, but if the same molecule were also synthesized naturally in a cell, the molecule synthesized naturally in the cell, e.g. 9-cis RA, would not be a processed molecule. Naturally occurring refers to pathways or molecules that have not been purposefully manipulated. The processed molecule can be further defined herein as comprising at least two residues, these residues may be the same or different. The first residues can be described as a "side-pocket 1 contacting" region. This portion of the processed molecule contributes to the contacts made with the side pocket 1, of the RXRα receptor defined by the amino acid residues Leu 436, Leu 433, Cys 432, Ile 310, Asn 306, Gly 429 and Trp 305 as present in SEQ ID NO: 1 or a subset of these amino acids: Leu 433, Ile 310, Asn 306, Gly 429 and Trp 305. The second residue of the processed molecule, referred to as the "RXR binding portion," is the remaining part of the molecule, excluding the side-pocket 1 contacting residue, that provides further contributing interactions with, for example, the RXRα. receptor. The RXR binding portion can optionally be divided into additional regions including a "cyclic organic residue" a polar binding portion and an organic binding portion." The cyclic organic residue can be directly attached to the side-pocket 1 contacting residue and one or both of the polar binding portion and/or the organic binding portion.

a) Interactions

The processed molecule contacts (interacts with) the RXR receptor. These contacts can occur at a number of places between the processed molecule and the RXR receptor, but must at least occur between the processed molecule and the side-pocket 1 of the RXR receptor. The sum of these contacts preferably are sufficient to reduce blood glucose levels and lower triglyreride levels in KKA$_y$ mice. One way of characterizing the interaction between the processed molecule and the RXR receptor is to assess how tightly the processed molecule and the RXR receptor bind. For example, the processed molecule and the RXR receptor can interact or bind each other with a $k_d$ of less than or equal to 1 μM. The binding can also preferably be defined by dissociation constants of less than or equal to 100 nM. The binding can also preferably be defined by dissociation constants of less than or equal to 10 nM. The binding can also be defined by dissociation constants of less than or equal to 1 nM. The binding can also preferably be defined by dissociation constants of less than or equal to 0.1 nM. It is understood that the dissociation constants are not completely controlled by the specific contacts that are made between the processed molecule and the side-pocket 1 of the RXR receptor. The contacts with the side-pocket 1 of the RXR receptor can contribute to the total affinity between the processed molecule and the RXR receptor but do not necessarily increase the affinity between the processed molecule and the RXR receptor.

b) Side Pocket Contacting Residue

The molecule has a side-pocket 1 contacting residue that is capable of contacting with a precise region of the RXR receptors defined as the side-pocket 1. This residue, present as one part of the processed molecule, can optionally be an alkyl, a substituted alkyl, a haloalkyl, an alkenyl, a substituted alkenyl, an alkynyl, a substituted alkynyl, a halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, oxime, O-substitued oxime, dialkylcarboxamide or substituted dialkylcarboxamide residue.

c) Structure

One way of characterizing the side-pocket 1 contacting residue is to quantify at the number of atoms that make up the side-pocket 1 contacting residue. The atoms must be connected. The side-pocket 1 contacting residue must have at least one connected atom. Optionally there are 2, 3, 4, 5, 6, 7, 8, 9, 10, 11, 12, 13, 14, 15, 16, 17, 18, 19, and 20 atoms or at least any one of these numbers of atoms. Optionally, embodiments may either have between 3 and 15 atoms, or 4 and 14 atoms, or 5 and 13 atoms, 6 and 12 atoms, 7 and 12 atoms, 8 and 12 atoms, 9 and 12 atoms, 10 and 12 atoms, 11 and 12 atoms, 5 and 6 atoms, 5 and 7 atoms, 5 and 8 atoms, 5 and 9 atoms, 5 and 10 atoms, 5 and 11 atoms, and 5 and 12 atoms.

Other embodiments can optionally comprise of greater than 1, 2, 3, 4, 5, 6, 7, 8, 9, 10, 11, 12, 13, 14, 15, 16, 17, 18, 19, and 20 connected atoms.

The side-pocket 1 contacting residue can consist of a number of different types of atoms. The connected atoms of the side-pocket 1 contacting residues can optionally include carbon, hydrogen, nitrogen, phosphorus, oxygen, sulfur, fluorine, chlorine, bromine, iodine, or mixtures thereof.

The side pocket contacting residues can optionally be, comprise, or contain an alkyl, a substituted alkyl, a haloalkyl, an alkenyl, a substituted alkenyl, an alkynyl, a substituted alkynyl, a halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, oxime, O-substitued oxime, dialkylcarboxamide or substituted dialkylcarboxamide residue.

The side-pocket 1 contacting residue can optionally be a haloalkoxy residue comprising 1 to 5 carbon atoms.

The RXR binding portion comprises a cyclic residue C comprising a substituted or unsubstituted C6–C18 aromatic ring residue wherein all ring atoms are carbon, a substituted or unsubstituted C2–C18 heteroaromatic ring residue having from one to three ring atoms selected from O, S, NE, NH, or a substituted or unsubstituted C2–C18 heteroaromatic ring residue having from one to three ring atoms selected from O, S, N, NH and N—R atoms or residues, wherein R comprises an alkyl, a substituted alkyl, an aryl, a substituted aryl, an acyl, a heteroaryl, or a substituted heteroaryl group.

The combination of side pocket contacting residue and the cyclic residue C comprises a residue of Formula (II), (III), (IV) or (V):

wherein R8, R9 and R10 are independently or together hydrogen, alkyl, substituted

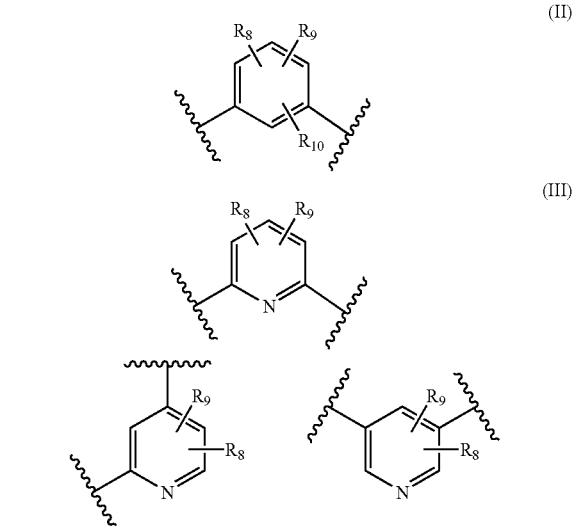

alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, oxime, O-substitued oxime, dialkylcarboxamide or substituted dialkylcarboxamide.

The cyclic residue C is connected to a polar binding residue comprising at least one functional group having at least one polar carbon-heteroatom or heteroatom-hydrogen bond.

In cone embodiment the polar binding residue comprises a residue of the formula:

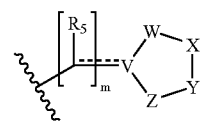

wherein a. m is an integer 0 or 1;

b. R5 is hydrogen, halogen, hydroxy, alkyl or substituted alkyl;

c. — — — — — represents a bond present or absent;

d. V=C or N;

e. W, X, Y and Z are independently or together —C(O)—, —C(S)—, —S—, —O— or —NH— residues. In one aspect of the invention V, W, X, Y, and Z together form a 2,4-thiazolidinedione, 2-thioxo-4-thiazolidinedione, isoxazolidinedione, 2,4-imidazolidinedione 2-thioxo-4-imidazolidinedione or [1,2,4]-oxadiazolidine-3,5-dione residue.

The cyclic residue C can be connected to residue D comprising a C4 to C25 substituted or unsubstituted hydrocarbon residue.

The cyclic residue C comprises the following formula:

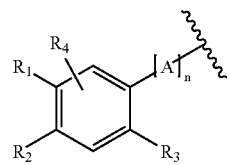

wherein:

n is independently 0 or 1;

R1 and R2 are 1) independently or together hydrogen, alkyl, substituted alkyl, haloalkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or 2) R1 and R2 together with the aromatic ring bonded thereto form a cycloalkyl, substituted cycloalkyl, cycloalkenyl or substituted cycloalkenyl residue that may optionally comprise 1 or 2 heteroatoms selected from O, S, NH or N-alkyl.

R3 and R4 are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide; and A is —CR6R7- where R6 and R7 are independently or together hydrogen, alkyl, substituted alkyl, alkoxy, substituted alkoxy or haloalkoxy; or R6 and R7 together form a cycloalkyl residue that may optionally comprise 1 or 2 heteroatoms selected from O, S, NH and N-alkyl.

d) Contact

A contact between the side pocket contacting residue and the side pocket can be defined by the distance or closeness of an atom of the side pocket contacting residue and any atom of one of the amino acid residues that make up the side pocket, as described in herein.

The number of contacts between the atoms of the side pocket containing residue and atoms of the side pocket 1 can vary for each RXR ligand. A contact is defined by the distance where the distance between the contacting atoms is less than 4 Angstrom (Å), e.g., 1, 1.5, 2, 2.5, 3, 3.5. Thus, when an atom of the side pocket contacting residue is within a distance of 1 to 4 Å of an atoms of side pocket 1, a contact is made and especially when the distance is 3,5 Å.

The number of contacts between the atoms of side-pocket 1 contacting residues of the processed molecule and the atoms of side-pocket 1 of the RXR receptor is one way to quantitate the interaction. To constitute an effective interaction between the side-pocket 1 contacting residue of a processed molecule with the RXR receptor there must be at least four contacts. Optionally, there are 4, 5, 6, 7, 8, 9, 10, 11, 12, 13, 14, 15, 16, 17, 18, 19, and 20 contacts or at least any one of these numbers of contacts. Preferred embodiments either have 7, 14, 15, 16, or 17 contacts or at least any number of these numbers of contacts.

Contacts can occur with any subset of the amino acids comprising side pocket 1, such as any subset of one or two or three or four or five or six of the amino acids in any combination.

For example, contacts preferably could be made with Leu 433, Ile 310, Asn 306, Gly 429 and Trp 305.

Contacts could also be made with, for example, the subsets Leu 436, Leu 433, Cys 432, Ile 310, Asn 306 or Gly 429 and Trp 305 Leu 436 or Leu 433, Cys 432, Ile 310, Asn 306, Gly 429 or Trp 305,Leu 433, Ile 310.

It is understood that any combination of the amino acids defining side pocket 1 can be used for contacts with the side pocket contacting residue.

In one preferred embodiment, disclosed are molecules that activate an RXR receptor to at least 60% of the activation of 9-cis retinoic acid, wherein the molecule comprises an RXR binding portion which binds the RXR receptor and comprises a side pocket contacting residue which has at least four contacts with the region consisting of Leu 433, Gly 429, Ile 310, Asn 306, and Trp 305 of side-pocket 1 of an RXR receptor, wherein the contacts are less than or equal to 3.5, Angstroms. Also provided are 5, 6, 7, 8, 9, 10, 11, 12, 13, 14, 15, 16, 17, 18, 19, and 20 contacts in this five amino acid region.

In another preferred embodiment, disclosed are molecules comprising an RXR receptor complexed with a molecule that activates an RXR receptor, wherein the molecule comprises an RXR binding portion which binds the RXR receptor and comprises a side pocket contacting residue which has at least four contacts with the region consisting of Leu 433, Gly 429, Ile 310, Asn 306, and Trp 305 of side-pocket 1 of an RXR receptor, wherein the contacts are less than or equal to 3.5 Angstroms. Also provided are 5, 6, 7, 8, 9, 10, 11, 12, 13, 14, 15, 16, 17, 18, 19, and 20 contacts in this five amino acid region.

In another preferred embodiment, disclosed are molecules that activate an RXR at least one fifth of the activity of compound 1 as measured in the adipocyte differentiation assay comprising an RXR binding portion which binds the RXR receptor and comprises a side pocket contacting residue which has at least four contacts with the region consisting of Leu 433, Gly 429, Ile 310. Asn 306, and Trp 305 of side-pocket 1 of an RXR receptor, wherein the contacts are less than or equal to 3.5 Angstroms. Also provided are 5, 6, 7, 8, 9, 10, 11, 12, 13, 14, 15, 16, 17, 18, 19, and 20 contacts in this five amino acid region.

As shown in the Examples, these seven amino acids that can form side-pocket 1 of a human RXR are typically arranged and positioned such that a small hydrophobic pocket or indentation is presented. For RXR alpha amino acids such as Leu 436, lie 310, Cys 432, Leu 433, Gly 429 and Trp 305 add to this hydrophobicity. Amino acids such as Asn 306 can also add to the total hydrophobicity of the side-pocket 1.

e) Activation of the RXR Receptor by the Molecules That Interact With the Receptor In some embodiments the compositions activate the RXR receptor with an EC 50 concentration less than or equal to 1 uM. Still other embodiments activate the RXR receptor with an EC 50 concentration less than or equal to 100 nM.

f) Molecules That are Produced by Selection Methods

Combinatorial chemistry includes but is not limited to all methods for isolating molecules that have specific activity, such as binding another molecule, and macromolecules that are capable of binding either a small molecule or another macromolecule.

Using methodology well known to those of skill in the art, in combination with various combinatorial libraries, one can isolate and characterize those molecules that bind to or interact with the desired target. The relative binding affinity of these compounds can be compared and optimum compounds identified using competitive binding studies that are well known to those of skill in the art. For example, the following are examples of various combinatorial compositions and methods which are herein incorporated by reference: U.S. Pat. Nos. 6,168,913; 5,565,324; 6,087,103; 6,060,596 and S. Brenner et al., "Encoded Combinatorial Chemistry", Proc. Natl. Acad. Sci. USA, vol. 89, (1992), pp. 5381–5383; R. W. Armstrong et al., "Microchip Encoded Combinatorial Libraries: Generation of a Spatially Encoded Library from a Pool Synthesis", Medicinal Chemistry, vol. 50, No. 6, (1996), pp. 258–260; J. J. Baldwin et al., "Synthesis of a Small Molecule Combinatorial Library Encoded with Molecular Tags", J. Am. Chem. Soc., vol. 117, (1995), pp. 5588–5589; H. P. Nestler et al., "A General Method for Molecular Tagging of Encoded Combinatorial Chemistry Libraires", J. Org. Chem., vol. 59, No. 17, (1994), pp. 4723–4724.

In some embodiments the processed molecules can also be produced by combinatorial chemistry and selection methods which are based on the disclosure that the claimed molecules all interact with a unique portion of the RXR receptor, side-pocket 1. The knowledge of this interaction means that molecules that interact with this side-pocket 1 of the RXR receptor can be isolated. The goal is to isolate those processed molecules that at least partially fill the side-pocket 1 region of the RXR receptor. In general this can be achieved by 1) interacting a library of molecules with an RXR receptor, 2) removing molecules that do not interact with the RXR receptor at a predetermined level, and 3) collecting the molecules that interact with side-pocket 1 of the RXR receptor.

Using methodology well known to those of skill in the art, in combination with various combinatorial libraries, one can isolate and characterize those compounds that bind to or interact with the desired target. The relative binding affinity of these compounds can be compared and optimum compounds identified using competitive binding studies which are well known to those of skill in the art.

g) Molecules That are Produced by Computer Selection Methods and Computer Assisted Design Another way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159–166; Ripka, New Scientist 54–57 (Jun. 16, 1988); McKinaly and Rossmann, 1989 Annu. Rev. Pharmacol. Toxiciol. 29, 111–122; Perry and Davies, QSAR: Quantitative Structure-Activity Relationships in Drug Design pp. 189–193 (Alan R. Liss, Inc. 1989); Lewis and Dean, 1989 Proc. R. Soc. Lond. 236, 125–140 and 141–162; and, with respect to a model enzyme for nucleic acid components., Askew, et al., 1989 J. Am. Chem. Soc. 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

3. Compounds

Disclosed are compounds of Formula (IX):

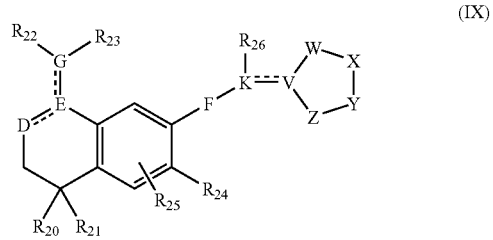

(IX)

wherein:

——— are independently or together present or absent;

D is CH or $CH_2$;

K is CH or a quaternary carbon;

G, E and V are independently a carbon or nitrogen atom;

F is of Formula (X), (XI), (XII) or (XIII)

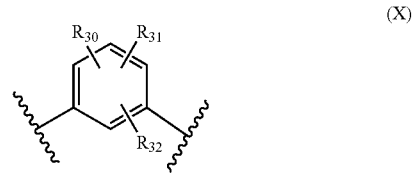

(X)

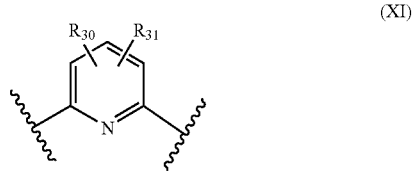

(XI)

-continued

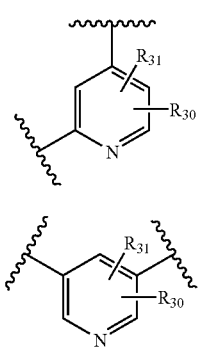

(XII)

(XIII)

wherein R$_{30}$, R$_{31}$ or R$_{32}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, thiohaloalkoxy, alkylsulfone, oxime, O-substituted oxime, dialkylcarboxamide or substituted dialkylcarboxamide;

R$_{20}$ and R$_{21}$ are independently or together hydrogen, alkyl, substituted alkyl;

R$_{22}$ is hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, trihaloalkyl, carboxy, carboalkoxy, alkylcarboxamide, substituted alkylcarboxamide, dialkylcarboxamide or substituted dialkylcarboxamide;

R$_{23}$ is absent, hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

R$_{22}$ and R$_{23}$ together form a cycloalkyl, substituted cycloalkyl, cycloalkenyl, substituted cycloalkenyl, aryl, substituted aryl, heteroaryl, substituted heteroaryl, heterocycle or substituted heterocycle.

R$_{24}$ and R$_{25}$ independently or together are hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

R$_{26}$ is hydrogen, halogen, hydroxy, alkyl or substituted alkyl; and

W, X, Y and Z are independently or together —C(O)—, —C(S)—, —S—, —O— or —NH— residues that together form a 2,4-thiazolidinedione, 2-thioxo-4-thiazolidinedione, isoxazolidinedione, 2,4-imidazolidinedione, [1,2,4]-oxadiazolidine-3,5-dione or 2-thioxo-4-imidazolidinedione residue; or pharmaceutically acceptable salts;

and do not have the structure of the Formula:

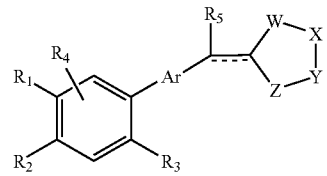

wherein:

R$_1$ and R$_2$ are 1) independently or together hydrogen, alkyl, substituted alkyl, haloalkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or 2) R$_1$ and R$_2$ together with the aromatic ring bonded thereto form a cycloalkyl, substituted cycloalkyl, cycloalkenyl or substituted cycloalkenyl residue that may optionally comprise 1 or 2 heteroatoms selected from O, S, NH or N-alkyl;

R$_3$ and R$_4$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

A is —CR$_6$R$_7$— where R6 and R7 are independently or together hydrogen, alkyl, substituted alkyl, alkoxy, substituted alkoxy or haloalkoxy; or R$_6$ and R$_7$ together form a cycloalkyl residue that may optionally comprise 1 or 2 heteroatoms selected from O, S, NH and N-alkyl;

Ar is Formula (II), (III), (IV) or (V):

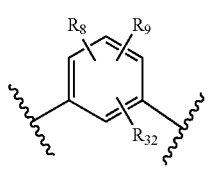

(II)

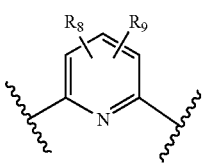

(III)

-continued

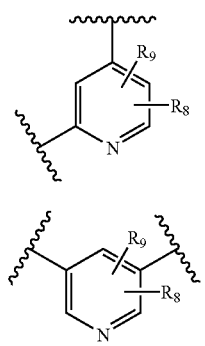

where $R_8$, $R_9$ and $R_{10}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

$R_5$ is hydrogen, halogen, hydroxy, alkyl or substituted alkyl;

————— represents a bond present or absent; and

W, X, Y and Z are independently or together —C(O)—, —C(S)—, —S—, —O— or —NH— residues that together form a 2,4-thiazolidinedione, 2-thioxo-4-thiazolidinedione, isoxazolidinedione, 2,4-imidazolidinedione or 2-thioxo-4-imidazolidinedione residue; or a pharmaceutically acceptable salt.

Also disclosed are compounds wherein F is Formula (X); $R_{20}$, $R_{21}$, and $R_{24}$ are independently or together alkyl or substituted alkyl; and $R_{30}$ is alkyl, substituted alkyl, haloalkoxy, amino, mono-substituted amino, di-substituted amino, thiohaloalkoxy, alkylsulfone, oxime or O-substituted oxime.

Also disclosed are compounds wherein $R_{20}$, $R_{21}$, and $R_{24}$ are independently or together alkyl or substituted alkyl; the bond between D and E is a double bond; the bond between E and G is a single bond; $R_{22}$ is hydrogen, alkyl or substituted alkyl; and $R_{23}$ is hydrogen, alkyl or substituted alkyl.

Also disclosed are compounds wherein $R_{20}$, $R_{21}$, and $R_{24}$ are independently or together alkyl or substituted alkyl; the bond between D and E is a double bond; the bond between E and G is a single bond; and $R_{22}$ and $R_{23}$ together form a cycloalkyl, substituted cycloalkyl, cycloalkenyl, substituted cycloalkenyl, aryl, substituted aryl, heteroaryl, substituted heteroaryl, heterocycle or substituted heterocycle.

Also disclosed are compounds wherein $R_{20}$, $R_{21}$, and $R_{24}$ are independently or together alkyl or substituted alkyl; the bond between D and E is a single bond; the bond between E and G is a double bond; $R_{22}$ is hydroxy or alkoxy; G is a nitrogen; and $R_{23}$ is absent.

Also disclosed are compounds wherein $R_{20}$, $R_{21}$, and $R_{24}$ are independently or together alkyl or substituted alkyl; the bond between D and E is a single bond; the bond between E and G is a double bond; $R_{22}$ and $R_{23}$ is together form a cycloalkyl, substituted cycloalkyl, cycloalkenyl, substituted cycloalkenyl, heterocycle or substituted heterocycle.

Also disclosed are compounds wherein $R_{20}$, $R_{21}$, and $R_{24}$ are independently or together alkyl or substituted alkyl; K is a quaternary carbon, the bond between K and V is a double bond; the bond between E and G is a double bond; $R_{22}$ is hydrogen, alkyl or substituted alkyl; G is a nitrogen; and $R_{23}$ is absent.

Also disclosed are compounds of Formula (100):

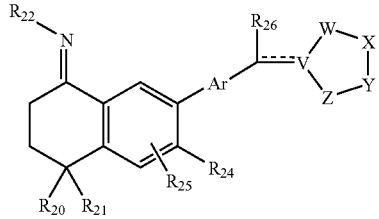

(100)
wherein:

————— represents a bond present or absent;

Ar is a substituted or unsubstituted benzene or pyridene ring;

$R_{20}$ and $R_{21}$ are independently selected from hydrogen or an alkyl or substituted alkyl residue comprising 1 to 8 carbon atoms;

$R_{22}$ is hydrogen, halogen, cyano, nitro, amino, or hydroxyl residue; or an alkyl, substituted alkyl, haloalkyl, alkenyl, substituted alkenyl, alkynyl, substituted alkynyl, acyloxy, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide residue comprising 1 to 8 carbon atoms, and $R_{22}$ may be oriented either syn or anti with respect to the compound; and $R_{24}$ and $R_{25}$ are independently selected from hydrogen, halogen, cyano, nitro, amino, or hydroxyl residue, or an alkyl, substituted alkyl, haloalkyl, alkenyl, substituted alkenyl, alkynyl, substituted alkynyl, acyloxy, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboximide, substituted alkylcarboxamide, dialkylcarboxamide or substituted dialkylcarboxamide residue comprising 1 to 8 carbon atoms;

$R_{26}$ is a hydrogen, halogen, or hydroxyl residue, or an alkyl or substituted alkyl comprising 1 to 4 carbon atoms;

V is a C or N atom, and W, X, Y and Z are independently selected from —C(O)—, —C(S)—, —S—, —O— or —NH— residues that together form a 2,4-thiazolidinedione, 2-thioxo-4-thiazolidinedione, isoxazolidinedione, 2,4-imidazolidinedione, [1,2,4]-oxadiazolidine-3,5-dione or 2-thioxo-4-imidazolidinedione residue; or a pharmaceutically acceptable salt thereof.

Then compound of claim 46 wherein Ar has the Formula (X), (XI), (XII) or (XIII)

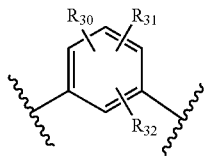

(X)

-continued

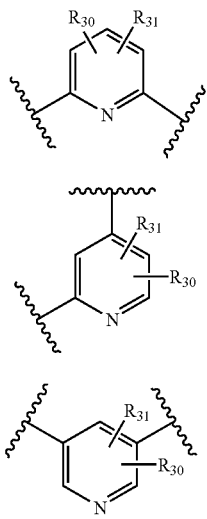

wherein $R_{30}$, $R_{31}$ or $R_{32}$ are independently selected from a hydrogen, halogen, cyano, nitro, amino, or hydroxyl residue, or an alkyl, substituted alkyl, haloalkyl, alkenyl, substituted alkenyl, alkynyl, substituted alkynyl, acyloxy, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, thiohaloalkoxy, alkylsulfone, oxime, O-substituted oxime, dialkylcarboxamide or substituted dialkylcarboxamide residue comprising 1 to 8 carbon atoms.

Also disclosed are compounds wherein at least one of $R_{30}$, $R_{31}$ or $R_{32}$ is not hydrogen.

Also disclosed are compounds which are processed molecules wherein Ar has the Formula

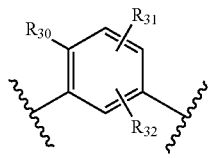

wherein $R_{30}$ is selected from an alkyl, substituted alkyl, haloalkoxy, amino, mono-substituted amino, di-substituted amino, thiohaloalkoxy, or alkylsulfone.

Disclosed are compounds wherein $R_{20}$, $R_{21}$ and $R_{24}$ are alkyl or substituted alkyl; ———— represents a bond present; and $R_{22}$ is hydroxy or an alkoxy residue having 1 to 4 carbon atoms.

The disclosed compounds are suitable for pharmaceutical compositions comprising one or more of the disclosed oxime compounds for administration in mammals for modulating lipid metabolism, carbohydrate metabolism, lipid and carbohydrate metabolism, or adipocyte differentiation. The compounds also can treat type 2 diabetes, polycystic ovary syndrome or syndrome X, type 2 diabetes, uncontrolled cellular proliferation, or cancer, such as, carcinoma, lymphoma, leukemia, or sarcoma, wherein the cancer is Hodgkin's Disease, myeloid leukemia, polycystic kidney disease, bladder cancer brain cancer, head and neck cancer, kidney cancer, lung cancer myeloma, neurolastoma/ glioblastoma, ovarian cancer, pancreatic cancer, prostate cancer, skin cancer, liver cancer, melanoma, colon cancer, cervical carcinoma, breast cancer epithelial cancer, and leukemia. Disclosed are compounds for administration in mammals that can also be used for treatment of an inflammatory disease, such as wherein the inflammatory disease is osteoarthritis, rheumatoid arthritis, Crohn's Disease, pulmonary fibrosis, or Inflammatory Bowel Disease.

Disclosed are methods of modulating lipid metabolism, carbohydrate metabolism, lipd and carbohydrate metabolism, or adipocyte differentiation comprising administering to a mammal diagnosed as needing such modulation pharmaceutical compositions disclosed herein, wherein the mammal is human for example. Disclosed are methods wherein the mammal is diagnosed as having type 2 diabetes.

Also disclosed are methods of treatment for a disease of uncontrolled cellular proliferation comprising administering to a mammal diagnosed as having a disease of uncontrolled proliferation, wherein for example, the mammal is human, and wherein for example, the mammal is diagnosed as having an inflammatory disease.

4. Pharmaceutical Compositions

Also provided are pharmaceutical compositions comprising the molecules of the invention. Pharmaceutical compositions are well known in the art. The pharmaceutical composition can treat a disease selected from the consisting of type 1 diabetes, type 2 diabetes, hypercholestermia, atherosclerosis, and related disorders. The composition of the invention can reduce blood glucose levels and lower triglyceride levels in $KKA_y$ mice.

B. Methods

1. Treating

The invention provides a method of treating a disease comprising administering a molecule that activates an RXR receptor, wherein the molecule comprises an RXR binding portion which binds the RXR receptor and comprises a side pocket contacting residue which contacts a side-pocket 1 of an RXR receptor. The disease can be selected from the group consisting of type 1 diabetes, type 2 diabetes, hypercholesteremia, atherosclerosis, and related disorders.

2. Screening

The invention also provides a method for selecting compositions that are RXR ligands which interact with side-pocket 1 of an RXR receptor comprising 1) interacting a library of molecules with an RXR receptor, 2) removing molecules that do not interact with the RXR receptor at a predetermined level, 3) collecting the molecules that interact with side-pocket 1 of the RXR receptor.

Also provided is a method of selecting compounds for the treatment of type 1 diabetes, type 2 diabetes, hypercholestermia or atherosclerosis comprising designing molecules to contact side pocket 1 of an RXR receptor. The-molecules can be designed to have four or more contacts, e.g. 4, 5, 6, 7, 8, 9, 10, 11, 12, 13, 14, 15, 16, 17, 18, 19 and 20; with a side pocket 1 of an RXR.

A compound that shows a good molecular modeling profile and has become a candidate for the subgroup of RXR ligands with unexpected properties which may make them useful for the treatment of type 2 diabetes and other diseases can be subsequently tested in the following in vitro and in vivo biological screens and testing models:

a) Adipocyte Differentiation Assay:

Prior to testing compounds in vivo, they can be run through the in vitro adipocyte differentiation assay based on the protocol of Zhang, et al. (1996) *Negative Regulation of Peroxisome Proliferator—Activated Receptor—γ Gene Expression Contributes to the Antiadipogenic effects of Tumor Necrosis Factor—α. Mol. Endo.* 10:1457–1456, incorporated herein by reference. In short, mouse 3T3-L1 preadipocytes are grown in culture medium containing 10% calf serum supplemented with antibiotics. Two days after reaching confluence, cells are treated with the selected compound at different concentrations dissolved in medium containing 10% fetal calf serum supplemented with antibiotics and kept at 10% $CO_2$. The test compounds are replaced every 2–3 days. Differentiation is assessed after 7 days of treatment by the lipid content in the cells, using the Triglyceride (INFINITY) reagent (Sigma Chemical, St. Louis, Mo.). If the test compound shows significant activity at $10^{-7}$ M and its activity is equal or no less than ⅕ that of compound 1 at $10^{-7}$ M, it is deemed suitable for testing in vivo.

b) RXR Agonist/Activator

RXR agonists activate the RXR receptor when interacting with RXR by binding to its binding pocket. This activation can be independent of whether the agonist, while interacting with portions of the ligand binding pocket, also interacts with side pocket 1. Activation, also often referred to as transcriptional activation, of RXR by agonists can be measured by a number of commonly used assays where the effect of the agonist ligand interacting with the RXR ligand binding pocket is to stimulate or induce transcription of a gene or genes in a cell. In one particular embodiment, transient transfection experiments (as described essentially by Zhang, et al. (1996) *Negative Regulation of Peroxisome Proliferator—Activated Receptor—γ Gene Expression Contributes to the Antiadipogenic effects of Tumor Necrosis Factor—α. Mol. Endo.* 10:1457–1456) can be used. In these cases, full length RXR proteins are expressed in living cells. Alternatively, hybrid proteins that contain a portion of another DNA binding domain and the ligand binding portion of the human RXRα receptor can be expressed in living cells instead of the full length RXR protein. Such hybrid proteins can bind to and activate specific reporter genes introduced into the same living cell and activation of such reporter genes is measured. The assays described here are very commonly used today by people skilled in the art of molecular biology experimenting. Transient transection assays are often used instead of ligand binding assays and can serve to measure or estimate an affinity of an RXR agonist ligand for RXR protein. The effective dose fifty ($ED_{50}$, also called $EC_{50}$) is the concentration of the ligand necessary to lead to one half maximal activation of the reporter gene in a living cell. Compounds that show 60% of the activity of the agonist 9-cis retenoic acid at $10^{-6}$ M can be considered an RXR activator/agonist. Compounds which show 70% 80% 90% of the activity of the agonist 9-cis retinoic acid are also provided.

c) Efficacy Testing in $KKA^y$

Antidiabetic activity of selected molecules can be demonstrated in the $KKA^y$ mouse, an animal model of type 2 diabetes (described in detail in Iwatsuka, et al., 1970 General Survey of Diabetic Features of Yellow KK Mice. *Endocrinol. Japon.* 17: 23–35, incorporated herein by reference). In short, adult diabetic $KKA^y$ mice are housed in a fixed 12—12-hr artificial light-dark cycle, and maintained on a standard rodent diet. Prior to commencing treatment, all of the animals are bled from the tail vein and serum levels of glucose and triglyceride are measured in duplicate. The animals are then sorted into different treatment groups with equal average triglyceride levels. The animals are treated with a single daily oral dose ranging from 3–30 mg/kg of the test compound suspended in sesame oil (dose volume of 3–5 ml/kg). Following one week of treatment the animals are bled from the tail vein and Serum glucose and triglycerides are measured in duplicate. Compounds showing efficacy in lowering glucose and which do not increase triglycerides or preferably, compounds that lower both glucose and triglyceride levels in this severely hypertriglyceridemic model, are preferably tested in further in vivo screen.

d) Toxicity in Wild Type Mice

Test compounds are tested in wild type mice at 10–100 times the efficacious dose in diabetic mice. Typically, adult male BALB/c mice are housed in a fixed 12—12-hr artificial light-dark cycle, and maintained on a standard rodent diet. The animals are treated with a single daily oral dose of the test compound suspended in sesame oil (dose volume of 5 ml/kg) as also described in the examples. Approximately two weeks later the animals are bled from the tail vein, then necropsied following sacrifice by carbon dioxide asphyxiation. Several serum biochemical parameters are measured. Of special significance is the effect the selected compounds have on serum triglyceride levels compared to vehicle treated control animals. If the compounds do not increase triglyceride levels even when used at multiples of the concentration at which they reduce glucose levels in $KKA^y$ mice, they can be preferably pursued in further drug development following procedures and tests typically used for such drug candidates in preclinical and clinical studies.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Computer Modeling

A requirement for a compound to be considered a candidate for the subclass of heterocyclic derivatives with unexpected properties which are useful for the treatment of disease such as type 2 diabetes, hypercholesteremia, osteosclerosis and other diseases is that these compounds can interact with a specific cavity, which is described herein as side pocket 1, in the ligand binding pocket of human RXRα, as described by Egea, et al in EMBO J Jun. 1, 2000 ;19(11):2592–601, incorporated herein by reference or as found in the PDB database (http:\\www.pdb.org). To determine whether the compound interacts with side pocket 1, computer modeling is used to dock putative ligands into three dimensional structure of the protein RXR. This is accomplished by 1: Representing the three dimensional coordinates of the protein as a set of x, y, and z coordinates specifying the centers of the atoms comprising the protein. 2. Representing a starting structure for the putative ligand by generating a conformation for the ligand in three dimensions that is consistent with bond lengths and atomic radii as specified by the atomic formula for the putative ligand. 3. Identifying torsional bonds within the ligand and the RXR protein as comprised of single bonds that are not a part of ring structures. 4. Moving and orienting the ligand with respect to the protein while simultaneously rotating the torsional bonds within the ligand, or simultaneously rotating the torsional bonds within both the ligand and the RXR protein, where the CA atoms of the protein are fixed. 5. Finding optimal fits of the ligand into the enclosed pocket of RXR using a scoring function that contains contributions from van der Waals and electrostatic interactions of the ligand with the protein. 6. Once an optimal docked conformation is obtained the ligand is evaluated to determine if its optimal docked structure interacts with side pocket 1 using a contact criterion outlined below in Example 2.

2. Example 2

Figure 1:
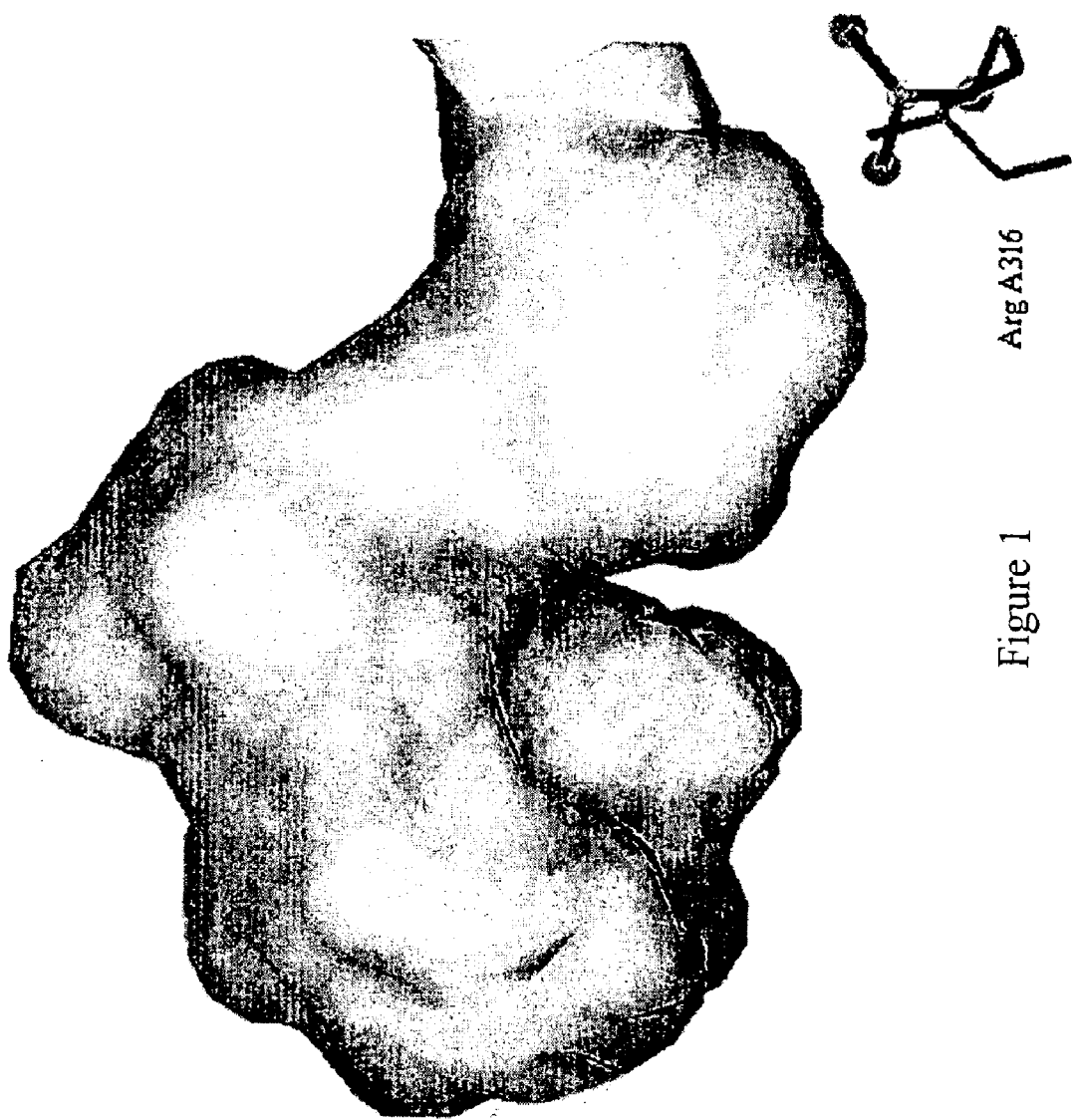
Figure 2:
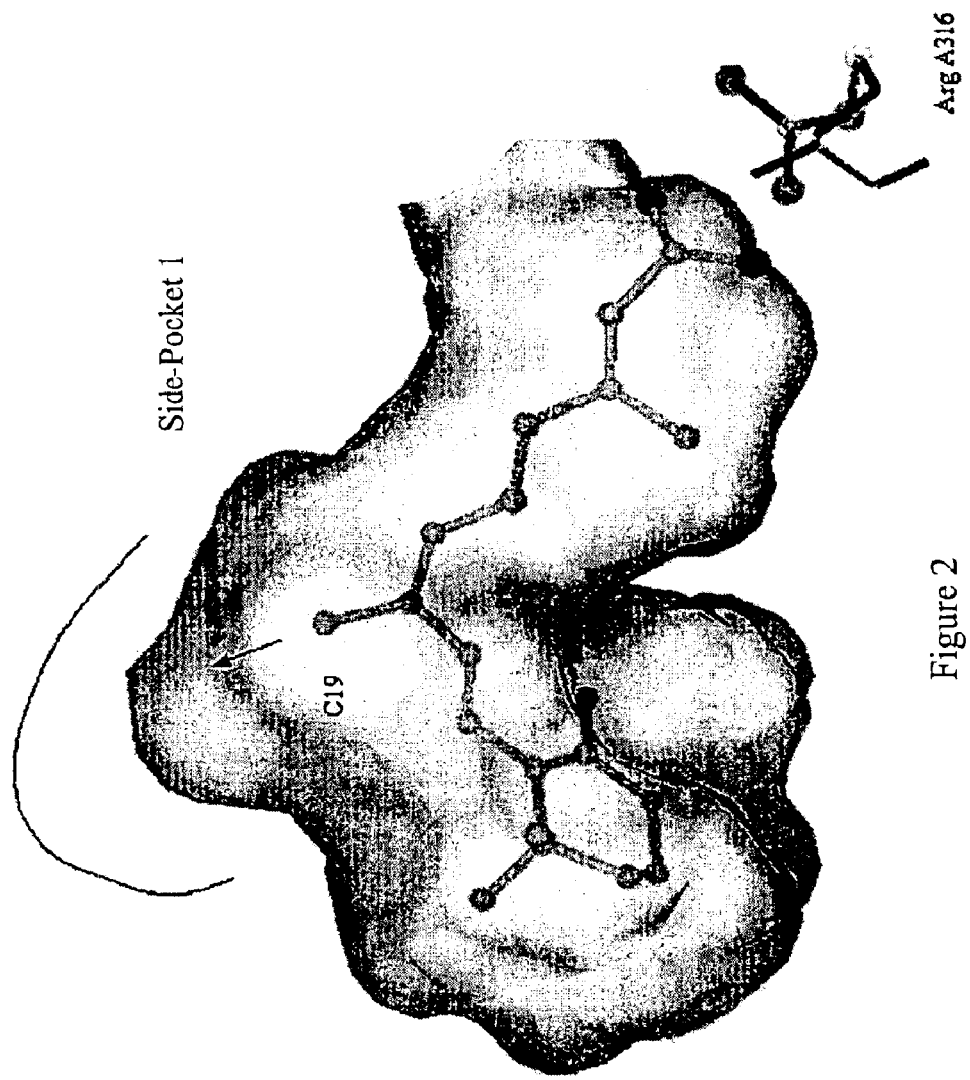
FIG. 2 shows that portion of the RXR ligand pocket that comprises side pocket 1, with reference to C19 of 9-cis-RA, a natural ligand of RXR (numbering as in 1FBY). While 9-cis-RA occupies a major portion of the RXR ligand pocket, side pocket 1 comprises unoccupied space in the crystal structure that is adjacent to C19.
Figure 4:
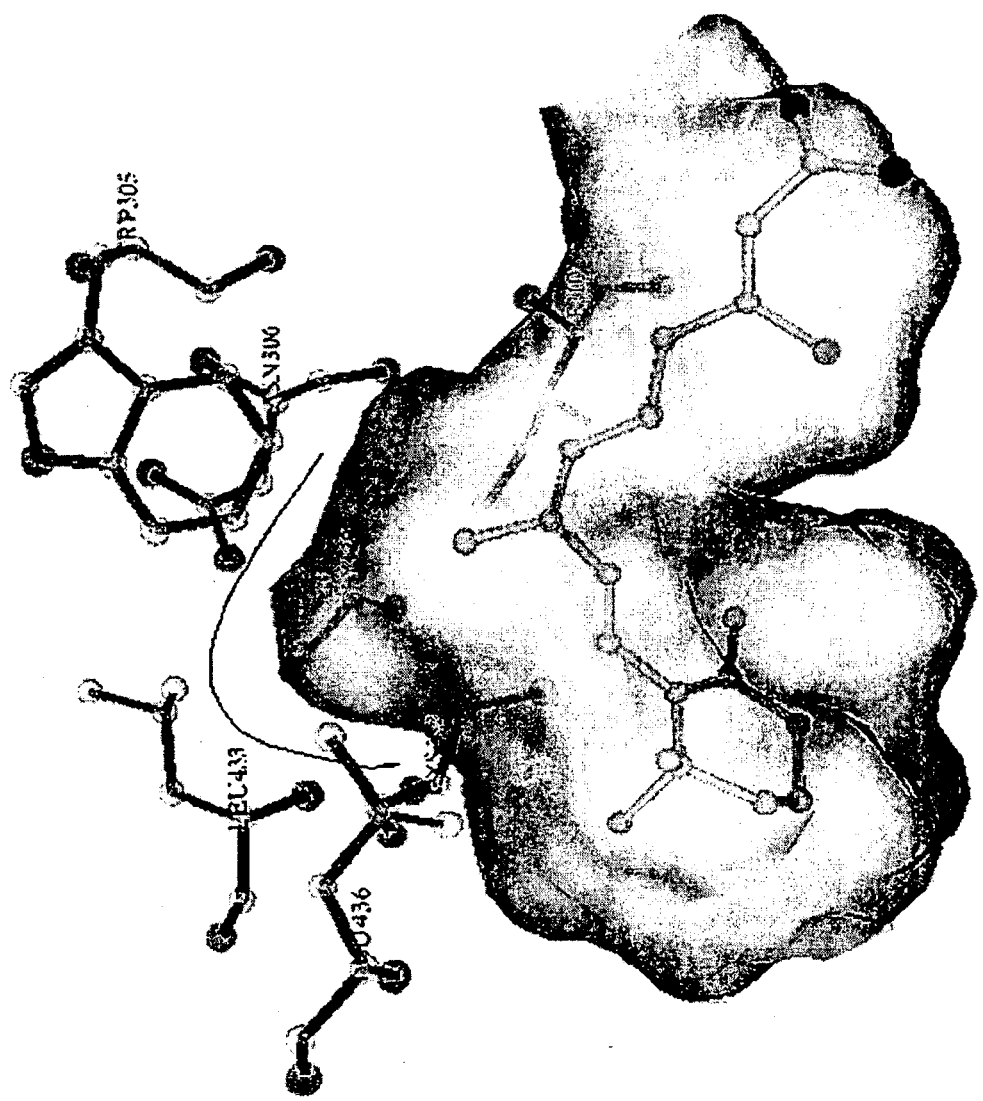
FIG. 4 shows the same view of FIG. 3 with the native ligand 9-cis-RA in the RXR ligand pocket site.

Evaluation of Interaction of a Compound with Side Pocket 1 and Candidacy to Belong to a Selected Subclass of RXR Ligands Useful for the Treatment of Diseases Side pocket 1 is defined using the protein coordinates of the crystal structure of human RXRα protein that has been determined and which has been deposited under 1FBY in the Protein Databank as further described in Example 1. Specifically, that portion of the protein coordinates of 1FBY that form side pocket 1 and more specifically, those atoms of the amino acids Trp A305, Asn A306, Ile A310, Cys A432, Gly A429, Leu A436, and Leu A433. Herein amino acids are specified using the three letter amino acid code to specify the amino acid type, while the amino acid sequence and sequence numbering scheme is as reported in the crystal structure 1FBY from the Protein Databank. The prefix A specifies that the A polypeptide chain from 1FBY is used. Specific atoms lining the side pocket 1 comprise a "Cavity 1 List" (C1L). C1L consists of Trp A305:CE3,CZ3,CH2; Asn A306:C,CA,CB,O; Ile A310:CD1; Cys A432: C,CB,O; Leu A436:CD1; Gly A429:O,C,CA, and Leu A433:N,CA, CD2, where individual atom names are defined as in 1FBY and are consistent with IUPAC-IUB naming conventions for amino acids with capital roman letters substituted for Greek letters. IUPAC-IUB Commission on Biochemical Nomenclature (1970). Abbreviations and symbols for the description of the conformation of polypeptide chains. J. Mol. Biol., 52, 1–17. The side pocket 1 formed by these atoms is illustrated in FIGS. 1–5. FIG. 1 shows the Connolly surface of the entire active site of RXR, with one amino acid Arg A316 shown for reference. The Connolly surface is generated as described in IUPAC-RUB Commission on Biochemical Nomenclature (1970). Abbreviations and symbols for the description of the conformation of polypeptide chains. J. Mol. Biol., 52, 1–17. FIG. 2 shows that portion of the RXR ligand pocket that comprises side pocket 1, with reference to C19 of 9-cis-RA, a natural ligand of RXR (numbering as in 1FBY). While 9-cis-RA occupies a major portion of the RXR ligand pocket, side pocket 1 comprises unoccupied space in the crystal structure that is adjacent to C19. FIG. 3 shows the amino acids lining side pocket 1; FIG. 4 shows the same view with the native ligand 9-cis-RA in the RXR ligand pocket site. FIG. 5 shows the same view with the compound 1 in the RXR ligand pocket. Note that compound 1 has a side pocket 1 contacting residue.

It is understood that the coordinates of the atoms making up the side pocket 1 can be obtained by using the coordinates of any other structures of an RXR, including structures of the side pocket 1.

FIG. 6 labels specific atoms from the amino acids shown in FIG. 3 that are close to the Connolly surface of the side pocket 1. In this figure, wherever connected atoms are selected, they are shown as lines connecting the atoms. Wherever isolated atoms are selected, these atoms are represented by stars. Where Association of the name and the atom requires, an arrow is provided pointing from the amino acid name to the individual atoms (as in, for example, Leu A436). The list of specific atoms are those of C1L.

As described in Example 1, when a candidate compound is evaluated, it is first docked into the protein structure using procedures described. Docked compounds are then selected as candidates for a special RXR ligand subclass, based on whether or not they enter the space defined as side pocket 1. This can be determined by evaluating the number of contacts—defined as NCCL—between ligand atoms and atoms in the C1L. NCCL is computed as follows. For each docked ligand a "Side Pocket 1 Contact List" (SPCL) is initialized to contain zero entries. For each non-hydrogen atom of the docked ligand all atoms in the C1L are examined. An atom from the C1L is added to the SPCL if the distance between the center of an atom of the side pocket contacting residue of the ligand and the center of an atom of C1L is lower than 4.0 Angstroms. When all atoms of the docked ligand have been examined the number NCCL of atoms added to the SPCL is computed. The docked ligand is considered a special RXR subclass candidate if NCCL of atoms added to the CCL list is greater than or equal to 4, which indicates that the docked ligand penetrates the side pocket 1 and interacts with the amino acids comprising it. Compound 1 (see FIGS. 5 and 7) and 3 satisfy this requirement and belong to the special RXR ligand subclass. Compound 2 (see FIG. 8) and compound 4 (see FIG. 9) do not fulfill these requirements.

[1] W. Welch, J. Ruppert, A. Jain, Hammerhead: Fast, Fully Automated Docking of Flexible Ligands to Protein Binding Sites, Chemistry and Biology 3: 449–462 1996.

Scoring Non-Covalent Ligand-Protein Interactions: A Continuous Differential Function Tuned to Compute Binding Affinities. A. N. Jain; Journal of Computer Aided Molecular Design 10:5, 427–440, 1996].

M. L. Connolly, "Solvent-accessible surfaces of proteins and nucleic acids," Science, 221, 709 (1983)

3. Example 3

Measuring Adipocyte Differentiation Activity

The ability of a compound to induce preadipocytes to differentiate into adipocytes is an indicator of its antidiabetic activity. This allows for screening many compounds in a simple in vitro assay, thus avoiding the task of testing all compounds in vivo. The adipocyte differentiation assay is based on the protocol of Zhang, et al. (1996) Negative Regulation of Peroxisome Proliferator-Activated Receptor-γ Gene Expression Contributes to the Antiadipogenic effects of Tumor Necrosis Factor—α. Mol. Endo. 10:1457–1456, incorporated herein by reference at least for material related to adipocyte differentiation assays. Mouse 3T3-L1 preadipocytes are grown in culture medium containing 10% calf serum supplemented with antibiotics. Two days after reaching confluence, cells are treated with the selected compound at different concentrations dissolved in medium containing 10% fetal calf serum supplemented with antibiotics and kept at 10% $CO_2$. The test compounds are replaced every 2–3 days. Differentiation is assessed after 7 days of treatment by the lipid content in the cells, using the Triglyceride (INFINITY) reagent (Sigma Chemical, St. Louis, Mo.) (see FIG. 15).

4. Example 4

RXR Activation

To confirm that the computer modeling/design of a compound does result in an RXR activator or RXR agonist, i.e.

a compound that leads to RXR activation or transcriptional activation, commonly used assays can be applied, where the effect of the agonist or activator, interacting with the RXR ligand binding pocket is to stimulate or induce transcription of a gene or genes in a cell. In one particular embodiment, transient transfection experiments (as described essentially by Zhang, et al. (1996) *Negative Regulation of Peroxisome Proliferator— Activated Receptor—γ Gene Expression Contributes to the Antiadipogenic effects of Tumor Necrosis Factor—α. Mol. Endo.* 10:1457–1456) can be used. In these cases, full length RXR proteins are expressed in living cells. Alternatively, hybrid proteins that contain a portion of another DNA, binding domain and the ligand binding portion of the human RXRα receptor can be expressed in living cells instead of the fall length RXR protein. Such hybrid proteins can bind to and activate specific reporter genes introduced into the same living cell and activation of such reporter genes is measured (Brand, A. H. & Perrimon, 1993, *Development*, 118:401–415; Moya-Camarena, S. Y. et.al., 1999, *J. Lipid Res.*, 40:1426:1433; Yi, Y. W. et al., 2000, *Biochem. Biophys. Res. Commun.*, 272:193–198, each are herein incorporated by reference at least for material related to reporter assays). These assays not only measure binding of the ligand to its target, which could also be measured by an in vitro binding assay, but also measure the agonistic or activator activity of the compound. In such an assay, new compounds are compared to a standard activator like compound I or the natural agonist of RXR: 9-cis retinoic acid (see Example 7). For instance, all compounds that show at a given concentration at least 60% of the activity of 9-cis retinoic acid can be considered useful activators.

5. Example 5

Measuring Antidiabetic Activity of a Selected Subclass of RXR Ligands

The antidiabetic activity of a selected subclass of RXR ligands can be demonstrated in the KKA$^y$ mouse, an animal model of type 2 diabetes (described in detail in Iwatsuka, et al., 1970 General Survey of Diabetic Features of Yellow KK Mice. Endocrinol. Japon. 17: 23–35, incorporated herein by reference). In this example, compound 1, which belongs to the novel subclass of RXR ligands is compared to a typical RXR ligand like compound 2 in the treatment of KKA$^y$ mice.

For this study, adult diabetic KKA$^y$ mice were housed in a fixed 12—12-hr artificial light-dark cycle, and maintained on a standard rodent diet. Prior to commencing treatment, all of the animals are bled from the tail vein and serum levels of glucose and triglyceride are measured in duplicate. The animals are then sorted into different treatment groups with equal average triglyceride levels. The animals are treated with a single daily oral dose of the test compound suspended in sesame oil (dose volume of 3 ml/kg).

Compound 1 shows a statistically significant decrease in both glucose and triglyceride levels following one and two weeks of treatment compared to vehicle treated control mice (See FIGS. 16 and 17 for data related to compound 7). By contrast, compound 2, which is known to lower glucose and triglyceride levels in type 2 diabetic db/db mice at the concentrations used here, failed to decrease glucose levels, and significantly increased triglyceride levels in KKA$^y$ mice following two weeks of treatment compared to vehicle treated controls (ANOVA, Fisher's LSD test; FIGS. 10, 11).

6. Example 6

Measuring Effect of a Selected Subclass of RXR Ligands on Triglyceride Levels in Mice Different classes of RXR compounds have different effects on wild type mice. Relevant to this document, is the effect of these molecules on serum triglyceride levels. In this example, compound 1, which belongs to the selected subclass of RXR ligands is compared to a typical RXR ligand like compound 2 in the treatment of wild type BALB/c mice.

For these studies, adult male BALB/c mice were housed in a fixed 12—12-hr artificial light-dark cycle, and maintained on a standard rodent diet. The animals were treated with a single daily oral dose of the test compound suspended in sesame oil (dose volume of 5 ml/kg).

Treatment with compound 1 at 10 and 30 mg/kg/day for 10 days (which represents approximately 30 to 100 fold excess over the dose that lowers glucose in diabetic db/db mice) does not change triglyceride levels compared to vehicle treated controls (FIG. 12). By contrast, treatment with Compound 2, when used at a similar excess over its effective glucose lowering dose in db/db, mice, causes a statistically significant, dose dependent increase in serum triglyceride levels compared to vehicle treated controls (ANOVA, Fisher's LSD test $p \leq 0.01$; FIG. 13**)

7. Example 7

Compounds Modeled as Disclosed Herein

The compound numbers refer to the compounds designated in FIG. 14.

TABLE 2

| Compound | Number of Contacts[1] | RXR Activation[2] | Differentiation Activity[3] | Efficacious in KKAy Mice[4] |
|---|---|---|---|---|
| 1 | 17 | 110% | 100% | Yes |
| 2 | 1 | >100% | >100% | No |
| 3 | 7 | 120% | 100% | Yes |
| 4 | 0 | >100% | >100% | No |
| 5 | 1 | >100% | >100% | No |
| 6 | 5 | >100% | >100% | No |
| 7 | 16 | 100% | 80% | Yes |
| 8 | 15 | 90% | 95% | Yes |
| 9 | 14 | 125% | 30% | Yes |

[1]The number of contacts between the side pocket contacting residue and side pocket 1, as described in Example 2.
[2]Activation of the RXR receptor by the test compounds when used at 1 μM compared to 9-cis-RA at equal concentration, as described in Example 4.
[3]The ability of the compound to induce the differentiation of pre-adipocytes to adipocytes when administered at 0.1 μM compared to Compound 1 when administered at an equal concentration, as described in Example 3.
[4]Only compounds that lower glucose without increasing triglycerides are considered efficacious, as described in Example 5.

8. Example 8

3-[(1-Oxo-4,4,6-trimethyl-1,2,3,4-tetrahydronaphthalene-7-yl)-O-methyloxime]-4-trifluoromethoxy-benzylidene-2,4-thiazolidinedione.

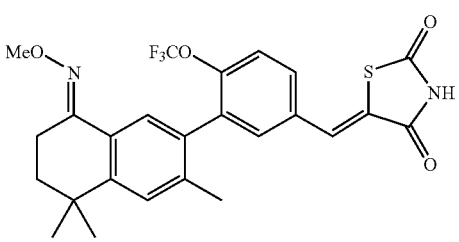

A mixture of toluene (5 mL), piperidine (38 μL), acetic acid (38 μL), 3-[(1-Oxo-4,4,6-trimethyl-1,2,3,4- tetrahydronaphthalene-7-yl)-O-methyloxime]-4-trifluoromethoxy-benzaldehyde (0.515 g, 1.271 mmol) and 2,4-thiazolidinedione (0.164 g, 1.398 mmol) was reflux overnight. The reaction mixture was cooled to room temperature, and the resulting crystalline compound was filtered then recrystallized from dichloromethane and hexane. The white solid was dried under high vacuum to afford 0.307 g (48%) of 3-[(1-Oxo-4,4,6-trimethyl-1,2,3,4-tetrahydronaphthalene-7-yl)-O-methyloxime]-4-trifluoromethoxy-benzylidene-2,4-thiazolidinedione, mp 224°. $^1$H NMR (300 MHz; DMSO-$d_6$): 1.29 (s, 6 H), 1.70 (t,J=5.6 Hz, 2 H), 2.11 (s, 3 H), 2.72 (t,J=5.6 Hz, 2 H), 3.86 (s, 3 H), 5.77 (s, 1 H), 7.40 (s, 1 H), 7.63 (s, 1 H), 7.66 (d, J=8.8 Hz, 1 H), 7.75 (d, J=8.8 Hz, 1 H), 7.87 (s, 1 H), 12.71 (brs, 1 H).

The intermediate 3-[(1-Oxo-4,4,6-trimethyl-1,2,3,4-tetrahydronaphthalene-7-yl)-O-methyloxime]-4-trifluoromethoxy-benzaldehyde was prepared as follows:

a) 3-[(1-Oxo-4,4,6-trimethyl-1,2,3,4-tetrahydronaphthalene-7-yl)-O-methyloxime]-4-trifluoromethoxy-benzaldehyde A mixture of 3-formyl-6-trifluoromethoxy-1-phenyl boronic acid (0.59 g, 2.52 mmol), 7-bromo-1-oxo-4,4,6-trimethyl-1,2,3,4-tetrahydronaphthalene-O-methyloxime (0.62 g, 2.10 mmol) and potassium carbonate (0.581 g, 4.20 mmol) in toluene (6.5 mL), ethanol (1.3 mL) and water (0.8 mL) was degassed with argon for 15 minutes. Tetrakis (triphenylphosphine)palladium(0) (0.049 g, 0.04 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was purified on silica gel [eluent: 10% ethyl acetate in hexane) to give 0.52 g of 3-[(1-oxo-4,4,6-trimethyl-1,2,3,4-tetrahydronaphthalene-7-yl)-O-methyloxime]-4-trifluoromethoxy-benzaldehyde (61%). $^1$H NMR (300 MHz; CDCl$_3$): 1.32 (s, 6 H), 1.75 (t, J=6.6 Hz, 2 H), 2.12 (s, 3 H), 2.79 (t, j=6.6 Hz, 2 H), 3.94 (s, 3 H), 7.24 (s, 1 H), 7.49 (d, J=8.4 Hz, 1 H), 7.77 (s, 1 H), 7.84 (d, J=2.1 Hz, 1 H), 7.93 (dd, J$_1$=2.1 Hz, J$_2$=8.7 Hz, 1 H), 10.02 (s, 1 H).

b) 3-Formyl-6-trifluoromethoxy-1-phenyl boronic acid

To a mixture of 2-(3-bromo-4-trifluoromethoxy)-1,3-dioxolane (7.20 g, 22.9 mmol) in THF (70 mL) cooled to −78° C. under an atmosphere of argon was added n-BuLi (13.8 mL, 2.5 M, 34.4 mmol) dropwise. The resulting suspension was stirred for 5 minutes and triisopropylborate (15.9 mL, 68.7 mmol) was added dropwise via syringe. The mixture was stirred at −50° C. for 2 hours then warmed up to room temperature and stirred overnight at room temperature. 1.0 N HCl (50 mL) was slowly added to the reaction mixture. After 3 hours the mixture was diluted with ethyl acetate and the layers separated, the aqueous layer was extracted once with ethyl acetate and the two organic layers combined. The resulting organic layer was washed with water, brine and dried (Mg$_2$SO$_4$). The mixture was filtered, evaporated and the residue stirred in hexane. The resulting white suspension was filtered and the white solid dried under high vacuum to afford 3.00 g of 3-formyl-6-trifluoromethoxy-1-phenyl boronic acid (56%) $^1$H NMR (300 MHz; DMSO-$d_6$+1 drop of D$_2$O): δ 7.55 (d, J=5.3 Hz, 1H); 8.07 (dd, J$_1$=1.1 Hz, J$_2$=5.3 Hz, 1 H); 10.07 (s, 1 H).

c) 2-(3-Bromo-4-trifluoromethoxy)-1,3-dioxolane

To a solution of 3-bromo-4-trifluoromethoxybenzaldehyde (ref; 20 g, 74.0 mmol) in toluene (200 L) was added ethylene glycol (82.6 mL, 1.48 mol) and p-toluenesulfonic acid monohydrate (0.84 g, 4.44 mmol). The reaction mixture was heated at reflux overnight and the water was removed using a Dean Stark apparatus. The solution was cooled to room temperature, poured into aqueous potassium carbonate (10%) and extracted with ethyl acetate. The organic layer was washed with water, brine and dried (Mg$_2$SO$_4$). The residue was purified on silica gel (eluent: 10% ethyl acetate in hexane) to give 15.4 g of 2-(3-bromo-4-trifluoromethoxy)-1,3-dioxolane (66%). $^1$H NMR (500 MHz; CDCl$_3$): δ 4.05 (m, 2 H); 4.11 (m, 2 H); 5.79 (s, 1 H); 7.32 (d, 1 H); 7.43 (d, 1 H); 7.77 (d, J=1.1 Hz, 1 H).

d) 7-Bromo-1-oxo-4,4,6-trimethyl-1,2,3,4-tetrahydronaphthalene-O-methyloxime

A solution of 7-bromo-1-oxo-4,4,6-trimethyl-1,2,3,4-tetrahydronaphthalene (1.02 g, 3.82 mmol), methoxyamine hydrochloride (0.638 mg, 7.63 mmol) and pyridine (0.93 mL, 11.46 mmol) in ethanol (30 mL) was refluxed for 3 hours. The mixture was concentrated in vacuo then diluted with water and extracted twice with ethyl acetate. The combined organic layer was dried (Mg$_2$SO$_4$), filtered and evaporated to give 1.13 g of 7-bromo-1-oxo-4,4,6-trimethyl-1,2,3,4-tetrahydronaphthalene-O-methyloxime as a yellow oil (quantitative) and used without further purification in the Suzuki coupling (step a). $^1$H NMR (300 MHz; CDCl$_3$): 1.25 (s, 6 H), 1.75 (t, J=6.9 Hz, 2 H), 2.38 (s, 3 H), 2.73 (t, J=6.9 Hz, 2 H), 3.98 (s, 3 H), 7.17 (s, 1 H), 8.11 (s, 1 H).

e) 7-Bromo-1-oxo-4,4,6-trimethyl-1,2,3,4-tetrahydronaphthalene

A solution of 1-oxo-4,4,6-trimethyl-1,2,3,4-tetrahydronaphthalene (40.0 g, 212 mmol) in dichloromethane (80 mL) was added dropwise at room temperature under argon with vigourous stiring to a suspension of aluminum chloride (56 g, 424 mmol) in dichloromethane (80 mL). Bromine (13 mL, 254 mmol) was then added slowly. The reaction mixture was stirred for 1.5 hours then poured into concentrated hydrochloride acid (6N, 300 mL) and extracted with ether. The organic layer was washed with water, aq NaHCO$_3$, water, brine and dried (Mg$_2$SO$_4$). The residue was purified on silica gel (eluent: 5 to 8% ethyl acetate in hexane) to give 32.2 g of 7-bromo-1-oxo-4,4,6-trimethyl-1,2,3,4-tetrahydronaphthalene (64%). $^1$H NMR (300 MHz; CDCl$_3$): 1.32 (s, 6 H), 1.94 (t, J=6.9 Hz, 2 H), 2.38 (s, 3 H), 2.64 (t, J=6.6 HZ, 2 H), 7.23 (s, 1 H), 8.06 (s, 1 H).

f) 1-Oxo-4,4,6-trimethyl-1,2,3,4-tetrahydronaphthalene

A solution of chromium(VI)oxide (86 g, 0.861 mol) in acetic acid (400 mL) and water (40 mL) was added dropwise to a stirred solution of 1,1,7-trimethyl-1,2,3,4-tetrahydronaphthalene in acetic acid (70 mL) and the reaction mixture stirred 2.5 hours at room temperature. Isopropanol (5 mL) was added and the whole concentrated in vacuo. The residue was dissolved in hexane and filtered over celite. The organic was washed with water and brine, dried (Mg$_2$SO$_4$), filtered and evaporated to give 40.3 g of 1-oxo-4,4,6-trimethyl-1,2,3,4-tetrahydronaphthalene and used without further purification in the bromination (step e). $^1$H NMR (300 MHz; CDCl$_3$): 1.36 (s, 6 H), 1.98 (t, J=6.9 Hz, 2 H), 2.38 (s, 3 H), 2.68 (t, J=6.9 Hz, 2 H), 7.01 (dd, J$_1$=0.6 Hz, J$_2$=7.9 Hz, 1 H), 7.19 (d, J=0.6 Hz, 1 H), 7.90 (d, J=8.1 Hz, 1 H).

g) 1,1,7-Trimethyl-1,2,3,4-tetrahydronaphthalene

A solution of 2-methyl-5-(p-tolyl)-3-pentanol (74 g, 0.385 mol) in dichloromethane (100 mL) was mixed with polyphosphoric acid (570 g) and the reaction mixture was heated to 60° C. and stirred overnight. After cooling, ice/water was slowly added and the aqueous extracted with dichloromethane. The organic layer was successively washed with water, aq NaHCO$_4$, water and brine, dried (Mg$_2$SO$_4$), filtered and evaporated to give 67 g of 1,1,7-trimethyl-1,2,3,4-tetrahydronaphthalene and used without further purification in the next step (step f). $^1$H NMR (300 MHz; CDCl$_3$): 1.34 (s, 6 H), 1.69 (m, 2 H), 1.83 (m, 2 H), 2.37 (s, 3 H), 2.78 (m, 2 H), 6.99 (m, 2 H), 7.19 (s, 1 H).

h) 2-Methyl-5-p-tolyl-3-pentanol

To a solution of trans-4-methyl-1-p-tolyl-1-penten-3-ol (43.2 g, 0.227 mol) in methanol (35 mL) was added 2 micro-spoon of palladium, 10% on activated carbon and the reaction mixture was hydrogenated overnight at 40 psi. The solution was diluted with ethyl acetate, filtered over celite and evaporated to give 40 g of 2-methyl-5-(p-tolyl)-3-pentanol as a colorless oil and used without further purification in the next step (step g). $^1$H NMR (300 MHz; CDCl$_3$): 0.90 (d, J=6.9 Hz, 6 H), 1.70 (m, 4 H), 2.31 (s, 3 H), 2.62 (m, 1 H), 2.78 (m, 1 H), 3.39 (m, 1 H), 7.09 (s, 4 H).

(l) trans-4-Methyl-1(p-tolyl)-1-penten-3-ol

To a solution of 4-methyl-1-p-tolyl-pent-1-en-3-one (77.0 g, 0.41 mol) in methanol (400 mL) was added slowly under argon sodium borohydride (31 g, 0.82 mol). The reaction was stirred at room temperature overnight and methanol (200 mL) was evaporated. The solution was neutralized with hydrochloric acid (2N), extracted with ethyl acetate. The organic layer was successively washed with water, aqueous NaHCO$_3$, water and brine, dried (Mg$_2$SO$_4$), filtered and evaporated to give 80.4 g of trans-4-methyl-1(p-tolyl)-1-penten-3-ol and used without further purification in the next step (step h). $^1$H NMR (300 MHz; CDCl$_3$): 0.94 (d, J=6.9 Hz, 3 H), 0.99 (d, J=6.6 Hz, 3 H), 1.83 (m, 1 H), 2.33 (s, 3 H), 4.01 (br, 1 H), 6.16 (dd, J$_1$=7.0 Hz, J$_2$=16.0 Hz, 1 H), 6.53 (d, J=16.0 Hz, 1 H), 7.12 (d, J=7.8 Hz, 1 H), 7.28 (d, J=7.8 Hz, 1 H).

(2) trans-4-Methyl-1-p-tolyl-pent-1-en-3-one

A solution of p-tolualdehyde (1 mL, 8.48 mmol), 3-methyl-2-butanone (1.81 mL, 16.96 mmol) and barium hydroxide (0.2 g, 1.17 mmol) in ethanol (4 mL) were mixed and the reaction mixture was heated at reflux for 1 hour. After cooling the solution was extracted with ethyl acetate. The organic layer was washed with water and brine, dried (Mg$_2$SO$_4$), filtered and evaporated to give 1.43 g of trans-4-methyl-1-p-tolyl-pent-1-en-3-one (90%) and used without further purification in the next step (step i). $^1$H NMR (300 MHz; CDCl$_3$): 1.16 (d, J=7.2 Hz, 6 H), 2.35 (s, 3 H), 2.92 (m, 1 H), 6.79 (dd, J=16.0 Hz, 1 H), 7.19 (d, J=7.5 Hz, 1 H), 7.43 (d, J=8.1 Hz, 1 H), 7.28 (d, J=16.2 Hz, 1 H).

9. Example 9

2-(3-[3,5,5,8,8-Pentamethyl-5,6,7,8-tetrahydronaphthyl-2-yl]-4-trifluoromethoxybenzyl)-[1,2,4]-oxadiazolidine-3,5-dione

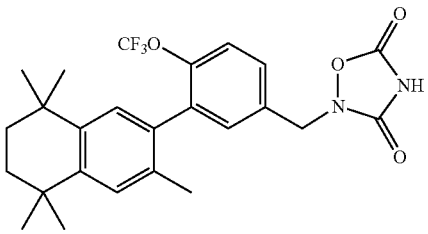

To a mixture of 3-(3,5,5,8,8-pentamethyl-5,6,7,8-tetrahydronaphthyl-2-yl)-4-trifluoromethoxybenzaldehyde (hydroxyoxime) (0.74 g, 1.8 mmol) in THF (5.0 mL) cooled to −10° C. was added N-(chlorocarbonyl)isocyanate (0.153 g, 1.45 mmol) dropwise. The mixture was stirred at 0° C. for 30 min and the reaction was quenched with 1 N HCl. The mixture was extracted with EtOAc, dried over MgSO$_4$ and filtered. The solvents were evaporated and the crude product was purified on silica gel (eluent: hexane:EtOAc, 20:1 to CH$_2$Cl$_2$:CH$_3$CN, 20:1 to 10:1) to give 0.28 g of 2-(3-[3,5,5,8,8-pentamethyl-5,6,7,8-tetrahydronaphthyl-2-yl]-4-trifluoromethoxybenzyl)-[1,2,4]-oxadiazolidine-3,5-dione as colorless oil. $^1$H NMR (300 MHz; DMSO-d$_6$): δ [1.20 (s), 1.27 (s), 12 H], 1.65 (s, 4 H), 2.00 (s, 3 H), 4.85 (s, 2 H), 7.04 (s, 1 H), 7.24 (s, 1 H), 7.33 (brs, 1 H), 7.45–7.52 (m, 2 H).

The intermediate 3-(3,5,5,8,8-pentamethyl-5,6,7,8-tetrahydronaphthyl-2-yl)-4-trifluoromethoxybenzaldehyde (hydroxyoxime) was prepared as follows:

a) 3-(3,5,5,8,8-Pentamethyl-5,6,7,8-tetrahydronaphthyl-2-yl)-4-trifluoromethoxybenzaldehyde (hydroxyoxime)

To a solution of 3-(3,5,5,8,8-pentamethyl-5,6,7,8-tetrahydronaphthyl-2-yl)-4-trifluoromethoxybenzaldehyde (0.781 g, 2.00 mmol) and trace amount of methyl orange in 10 mL of MeOH:THF (1:1) was added an aqueous solution of hydroxyamine hydrochloride (0.174 g, 2.5 mmol) at room temperature. The mixture was adjusted to pH=9 with 6 N KOH and additional MeOH:THF (1:1) was added. To the resulting homogeneous solution was added solid sodium cyanoborohydride (0.126 g, 2.00 mmol) followed by addition of 2.0 N HCl in aqueous MeOH until the mixture turned ruby red. Additional acid was added to maintain the color during the course of the reaction. After 22 hours, the organics were removed under reduced vacuum and the resulting aqueous solution was adjusted to pH=12 with 2 N KOH. The mixture was extracted with CH$_2$Cl$_2$, washed with brine and dried over MgSO$_4$. The mixture was filtered, evaporated and the resulting white solid dried under high vacuum to give 0.74 g of 3-(3,5,5,8,8-pentamethyl-5,6,7,8-tetrahydronaphthyl-2-yl)-4-trifluoromethoxybenzaldehyde (hydroxyoxime). Used without further purification.

b) 3-(3,5,5,8,8-Pentamethyl-5,6,7,8-tetrahydronaphthyl-2-yl)-4-trifluoromethoxybenzaldehyde To a solution of 3-bromo-4-trifluoromethoxybenzaldehyde (10.0 g, 37.2 mmol), (3,5,5,8,8-pentamethyl-5,6,7,8-tetrahydronaphthalen-2-yl) boronic acid (11 g, 44.68 mmol, 1.2 eq) in a mixture of toluene (100 mL), ethanol (20 mL) and water (15 mL) was added potassium carbonate (10.28 g, 74.4 mmol, 2 eq). The solution was degassed with argon for 40 minutes. Tetrakis (triphenylphosphine)palladium(0) (0.86 g, 0.74 mmol, 0.02 eq) was added and the mixture heated at reflux under argon for 22 hours. The solution was cooled to room temperature, diluted with ethyl acetate and washed successively with water and brine, dried over MgSO$_4$, filtered and evaporated. The residue was chromatographed on silica gel (silica: 70-230 mesh, 60A, 400 g, eluant: ethyl acetate/hexane, 5:95) to give 4-trifluoromethoxy-3-(3,5,5,8,7-pentamethyl-5,6,7,8-tetrahydronaphthalen-2-yl) benzaldehyde (11.1 g, 76%). $^1$H NMR (300 MHz; CDCl$_3$) 1.25 (s, 6H); 1.32 (s, 6H); 1.70 (s, 4H); 2.08 (s, 3H); 7.06 (s, 1H); 7.18 (s, 1H); 7.48 (dd, J$_1$=8.4 Hz, J$_2$=1.5 Hz, 1H); 7.84 (d, J=2.0 Hz, 1H); 7.88 (dd, J$_1$=2.0 Hz, J$_2$=8.5 Hz 1H), 9.91 (s, 1H)

c) 3-Bromo-4-trifluoromethoxybenzaldehyde

To a solution of 4-trifluoromethoxybenzaldehyde (215 g, 1.13 mol) in a mixture of TFA (300 mL), CH$_2$Cl$_2$ (300 mL) and H$_2$SO$_4$ (150 mL) was added at room temperature N-bromosuccinimide (402 g, 2.26 mol) in equal portion over 7 hours. The reaction mixture was stirred for 4 days at room temperature, poured into ice-water and extracted with CH$_2$Cl$_2$ The organic layer was washed with water then treated with saturated NaHCO$_3$ (1.5 L) for 2 hrs. The layers were separated and the organic layer further washed with water and brine, dried over MgSO$_4$, filtered and evaporated. The residue was triturated with hexane and filtered. After evaporation of the solvent, the residue was distilled to give 3-bromo-4-trifluoromethoxybenzaldehyde (190.2 g, 81° C., 1.0 mm/Hg, 62%).

10. Example 10

5-[3-(1-Ethyl-4,4,6-trimethyl-2-oxo-1,2,3,4-tetrahydro-quinolin-7-yl)-4-trifluoromethoxy-benzylidene]-thiazolidine-2,4-dione, which may be referred to as "Compound 8 in Table 2

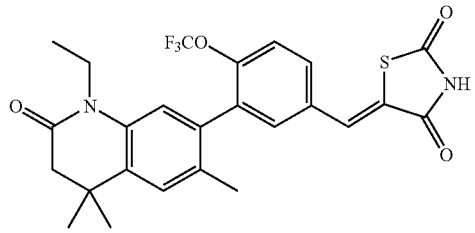

Prepared in a similar manner to example 1 using 3-(1-Ethyl-4,4,6-trimethyl-2-oxo-1,2,3,4-tetrahydro-quinolin-7-yl)-4-trifluoromethoxy-benzaldehyde. 56% yield after column chromatography on silica gel (40% ethyl acetate in hexane). mp 156–154° C. $^1$H-NMR (300 MHz, DMSO-d-6): 1.06 (t, J=7.5 Hz, 3 H); 1.26 (s, 6 H), 2.08 (s, 3 H), 2.46 (s, 2 H), 3.95 (br d, 2 H), 6.97 (s, 1 H), 7.31 (s, 1 H), 7.65 (s, 1 H), 7.66 (dd, J=1.5 Hz and 9 Hz, 1 H), 7.75 (dd, J=2.4 Hz and 8.7 Hz, 1 H), 7.87 (s, 1H), 12.71 (br s, 1 H).

The intermediate 3-(1-Ethyl-4,4,6-trimethyl-2-oxo-1,2,3,4-tetrahydro-quinolin-7-yl)-4-trifluoromethoxy-benzaldehyde was prepared as follows:

a) 3-(1-Ethyl-4,4,6-trimethyl-2-oxo-1,2,3,4-tetrahydro-quinolin-7-yl)-4-trifluoromethoxy-benzaldehyde A mixture of 3-formyl-6-trifluoromethoxy-1-phenyl boronic acid (Example f below) (8.2 g, 34.84 mmol), 7-bromo-1-ethyl-4,4,6-trimethyl-3,4-dihydro-1H-quinoline-2-one (8.6 g, 29.03 mmol, Example b) and potassium carbonate (8 g, 58.06 mmol) in toluene (80 mL), ethanol (16 mL) and water (12 mL) was degassed with argon for 30 minutes. Tetrakis(triphenylphosphine)palladium(0) (1.34 g, 0.04 mmol) was added and the mixture heated at reflux under argon for 48 hrs. The solution was cooled to room temperature, diluted with ethyl acetate and washed successively with water and brine, dried over anhydrous magnesium sulfate, filtered and evaporated. The residue was purified on silica gel (30% ethyl acetate in hexane) to give 6.66 g of 3-(1-ethyl-4,4,6-trimethyl-2-oxo-1,2,3,4-tetrahydro-quinolin-7-yl)-4-trifluoromethoxy-benzaldehyde (57%). $^1$H NMR (300 MHz; CDCl$_3$): 1.20 (t, J=7.2 Hz, 3 H), 1.33 (s, 6 H), 1.62 (s, 3 H), 2.10 (s, 3 H), 2.53 (s, 2 H), 400 (br d, 2 H), 6.81 (s, 1 H), 7.19 (s, 1 H), 7.55 (dd, J=1.8 and 8.4 Hz, 1 H), 7.85 (d, J=2.4 Hz, 1 H), 7.97 (dd, J=2.1 and 8.4 Hz, 1 H), 10.05 (s, 1 H).

(1) 7-bromo-1-ethyl-4,4,6-trimethyl-3,4-dihydro-1H-quinoline-2-one.

A mixture of powdered potassium hydroxide (3.35 g, 59.67 mmol) in DMSO (40 mL) was stirred at 0° C. for 10 min. 7-bromo-4,4,6-trimethyl-3,4-dihydro-1H-quinoline-2-one (Example 2c) (8.0 g, 29.83 mmol) was added cautiously, followed immediately by the addition of ethyl iodide (12 mL, 149.17 mmol). The reaction mixture was kept at 0° C. for 30 min then slowly warmed up to room temperature and stirred overnight at room temperature. The reaction mixture was poured into water and extracted with dichloromethane washed with water and brine, dried (Mg$_2$SO$_4$), filtered and evaporated to give 8.8 g of 7-bromo-1,4,4,6-tetramethyl-3,4-dihydro-1H-quinoline-2-one and used without further purification in the Suzuki coupling (step a). $^1$H NMR (300 MHz; CDCl$_3$): 1.24 (t, J=7.2 Hz, 1 H), 1.25 (s, 6 H), 2.37 (s, 3 H), 2.45 (s, 2 H), 3.98 (q, 2 H), 7.13 (s, 1 H), 7.18 (s, 1 H).

(2) 7-bromo-4,4,6-trimethyl-3,4-dihydro-1H-quinoline-2-one.

To a solution of 3-methyl-but-2-enoic acid (3-bromo-4-methyl-phenyl)-amide (70.0 g, 261 mmol, Example d) at 90° C. was added portion wise, under argon, with vigorous stirring aluminum chloride (52.3 g, 391 mmol) over 1.5 hr. The reaction mixture was stirred for 2 hours at 110–120° C. The reaction mixture was cooled to room temperature and ice-water was carefully added. The solution was extracted with dichloromethane and the organic washed with 2N HCl, water, saturated aqueous NaHCO$_3$, water and brine, dried (Mg$_2$SO$_4$), filtered and evaporated. The residue was crystallized from dichloromethane/hexane to give 46 g of 7-bromo-4,4,6-trimethyl-3,4-dihydro-1H-quinoline-2-one. The mother liquor was further chromatographed on silica gel(20% ethyl acetate in hexane) to give 6.2 g more of product. (75%). $^1$H NMR (300 MHz; CDCl$_3$): 1.30 (s, 6 H), 2.33 (s, 3 H), 2.46 (s, 2 H), 7.07 (s, 1 H), 7.10 (s, 1 H), 9.87 (br s, 1 H).

(3) 3-Methyl-but-2-enoic acid (3-bromo-4-methyl-phenyl)-amide.

To a biphasic mixture of 3-bromo-4-methylaniline (50 g, 0.269 mol, Example e), 10% NaOH (270 mL) and dichloromethane (160 mL) was added dropwise over a period of 2 hours 3,3-dimethylacryloyl chloride (36 mL, 0.322 mol) in dichloromethane (95 mL). The solution was stirred at room temperature for 48 hours then diluted with water (100 mL).

The aqueous layer was further extracted with dichloromethane. The organic layers were combined and washed with water and brine, dried (Mg$_2$SO$_4$), filtered and evaporated. The white solid was triturated with hexane and collected to give 70 g (97%) of 3-Methyl-but-2-enoic acid (3-bromo-4-methyl-phenyl)-amide. $^1$H NMR (300 MHz; CDCl$_3$): 1.89 (s, 3 H), 2.21 (s, 3 H), 2.33 (s, 3 H), 5.68 (s, 1 H), 7.14 (d, J=8.0 Hz, 1 H), 7.17 (br s, 1 H), 7.33 (d, J=8.0 Hz, 1 H), 7.79 (s, 1 H).

(4) 3-bromo-4-methylaniline.

To a solution of 2-bromo-4-nitrotoluene (50 g, 0.231 mol in ethylacetate (330 mL) and Ethanol (150 mL) was added Tin(II)chloride dihydrate (208 g, 0.924 mol) portionwise. The reaction mixture was stirred at room temperature overnight. The solution was then treated with potassium carbonate until pH=7 and filtered over celite. The filtrate was washed with water, aqueous NaHCO$_3$, water and brine, dried (Mg$_2$SO$_4$), filtered and evaporated to give 42.71 g (100%) of 3-bromo-4-methylaniline. $^1$H NMR (300 MHz; CDCl$_3$): 2.27 (s, 3 H), 3.57 (br s, 2 H), 6.54 (dd, J=2.7 Hz and 8.1 Hz, 1 H), 6.90 (d, J=2.1 Hz, 1 H), 6.98 (d, J=8.1 H).

(5) 3-formyl-6-trifluoromethoxy-1-phenyl boronic acid.

To a mixture of 2-(3-bromo-4-trifluoromethoxy-1-phenyl)-1,3-dioxolane (7.20 g, 22.9 mmol, Example g below) in THF (70 mL) cooled to −78° C. under an atmosphere of argon was added n-BuLi (13.8 mL, 2.5 M, 34.4 mmol) dropwise. The resulting suspension was stirred for 5 minutes and triisopropylborate (15.9 mL, 68.7 mmol) was added dropwise via syringe. The mixture was stirred at −50° C. for 2 hours then warmed up to room temperature and stirred overnight at room temperature. 1.0 N HCl (50 mL) was slowly added to the reaction mixture. After 3 hours the mixture was diluted with ethyl acetate and the layers separated, the aqueous layer was extracted once with ethyl acetate and the two organic layers combined. The resulting organic layer was washed with water, brine and dried (Mg$_2$SO$_4$). The mixture was filtered, evaporated and the residue stirred in hexane. The resulting white suspension was filtered and the white solid dried under high vacuum to afford 3.00 g of 3-formyl-6-trifluoromethoxy-1-phenyl boronic acid (56%). $^1$H NMR (300 MHz; CDCL$_3$): δ 7.42 (d, J=7.0 Hz, 1 H), 8.07 (dd, J$_1$=2.1 Hz, J$_2$=8.7 Hz, 1 H), 8.47 (d, J=1.8 Hz, 1 H), 10.05 (s, 1 H).

(6) 2-(3-bromo-4-trifluoromethoxy-1-phenyl)-1,3-dioxolane.

To a solution of 3-bromo-4-trifluoromethoxybenzaldehyde (20 g, 74.0 mmol) in toluene (200 mL) was added ethylene glycol (82.6 mL, 1.48 mol) and p-toluenesulfonic acid monohydrate (0.84 g, 4.44 mmol). The reaction mixture was heated at reflux overnight and the water was removed using a Dean Stark apparatus. The solution was cooled to room temperature, poured into aqueous potassium carbonate (10%) and extracted with ethyl acetate. The organic layer was washed with water, brine and dried (Mg$_2$SO$_4$). The residue was purified on silica gel (eluent: 10% ethyl acetate in hexane) to give 15.4 g of 2-(3-bromo-4-trifluoromethoxy)-1,3-dioxolane (66%). $^1$H NMR (500 MHz; CDCl$_3$): δ 4.05 (m, 2 H), 4.11 (m, 2 H), 5.79 (s, 1 H), 7.32 (d, 1 H), 7.43 (d, 1 H), 7.77 (d, J=1.1 Hz, 1 H).

11. Example 11

5-[4-Dimethylamino-3-(8-methoxyimino-3,5,5-trimethyl-5,6,7,8-tetrahydro-naphthalen-2-yl)-benzylidene]-thiazolidine-2,4-dione

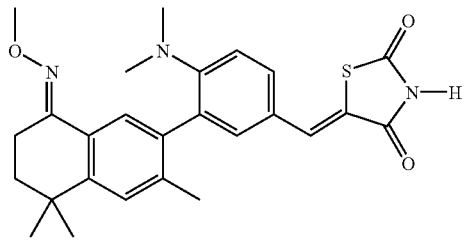

Prepared in a similar manner to example 1. mp 254–256° C. (300 MHz, DMSO) 1.27 (2 s, 6 H), 1.92 (t, J=6.6 Hz, 2H), 2.11 (s, 3 H), 2.56 (s, 6 H), 2.70 (t, J=6.6 Hz, 2 H), 3.86 (s, 3 H), 7.10 (d, J=9 Hz, 1 H), 7.22 (d, J=1.8 Hz, 1 H), 7.34 (s, 1 H), 7.49 (dd, J$_1$=1.8 Hz, J$_2$=8.7 Hz, 1 H), 7.68 (s, 1 H), 7.73 (s, 1 H), 12.44 (br s, 1H).

12. Example 12

5-[4–Chloro-3-(8-methoxyimino-3,5,5-trimethyl-5,6,7,8-tetrahydro-naphthalen-2-yl)-benzylidene]-thiazolidine-2,4-dione

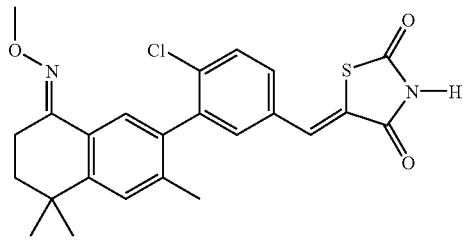

Prepared in a similar manner to example 1. mp 252–254° C. (300 MHz, DMSO) 1.29 (s, 6 H), 1.70 (t, 2 H), 2.08 (s, 3 H), 2.71 (t, 2 H), 3.86 (s, 3 H), 7.40 (s, 1 H), 7.54 (s, 1 H), 7.59 (s, 1 H), 7.62 (d, J=8.4 Hz, 1 H), 7.75 (d, J=8.4 Hz, 1 H), 7.83 (s, 1 H), 12.68 (br s, 1 H).

D. References

Iwatsuka H., Shino A., and Suzuoki Z. (I1970) General Survey of Diabetic Features of Yellow KK Mice. *Endocrinol Japon.* 17: 23–35.

E. Sequences

SEQ ID NO: 1 RXR alpha

SEQ ID NO: 2 RXR Beta

SEQ ID NO: 3 RXR gamma

What is claimed is:

1. A compound of Formula (100):

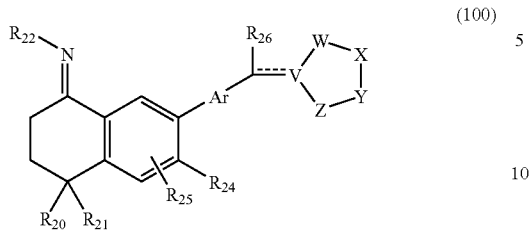

wherein:

——— represents a bond present or absent;

Ar is a substituted or unsubstituted benzene or pyridine ring;

$R_{20}$ and $R_{21}$ are independently selected from hydrogen or an alkyl an substituted alkyl group comprising 1 to 8 carbon atoms;

$R_{22}$ is hydrogen, halogen, cyano, nitro, amino, or hydroxyl residue; or an alkyl, substituted alkyl, haloalkyl, alkenyl, substituted alkenyl, alkynyl, substituted alkynyl, acyloxy, mono-substituted amino, di-substituted amino, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide group comprising 1 to 8 carbon atoms, an $R_{22}$ may be oriented either syn or anti with respect to the compound; and $R_{24}$ and $R_{25}$ are independently selected from hydrogen, halogen, cyano, nitro, amino, or hydroxyl group, or an alkyl, substituted alkyl, haloalkyl, alkenyl, substituted alkenyl, alkynyl, substituted alkynyl, acyloxy, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide and substituted dialkylcarboxamide group comprising 1 to 8 carbon atoms;

$R_{26}$ is a hydrogen, halogen, or hydroxyl group, or an alkyl or substituted alkyl group comprising 1 to 4 carbon atoms;

V is a C or N atom, and W, X, Y and Z together form a 2,4-thiazolidinedione, 2-thioxo-4-thiazolidinedione, isoxazolidinedione, 2,4-imidazolidinedione, [1,2,4]-oxadiazolidine-3,5-dione or 2-thioxo-4-imidazolidinedione group; or a pharmaceutically acceptable salt thereof.

2. The compound of claim 1, wherein Ar has the Formula (X), (XI), (XII) or (XIII)

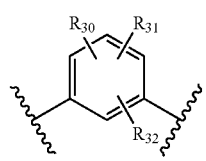

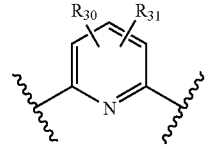

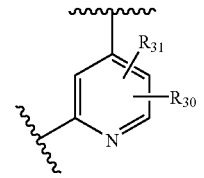

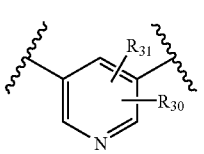

wherein $R_{30}$, $R_{31}$ or $R_{32}$ are independently selected from a hydrogen, halogen, cyano, nitro, amino, or hydroxyl residue, or an alkyl, substituted alkyl, haloalkyl, alkenyl, substituted alkenyl, alkynyl, substituted alkynyl, acyloxy, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy thioalkyl, thiohaloalkyl, carboxy, carboalkoxy, alkylcarboxamide, substituted alkylcarboxamide, thiohaloalkoxy, alkylsulfone, oxime, O-substituted oxime, dialkylcarboxamide and substituted dialkylcarboxamide group comprising 1 to 8 carbon atoms.

3. The compound of claim 1 wherein at least one of $R_{30}$, $R_{31}$ or $R_{32}$ is not hydrogen.

4. The compound of claim 1 wherein Ar has the Formula

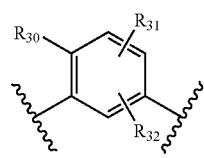

wherein $R_{30}$ is selected from an alkyl, substituted alkyl, haloalkoxy, amino, mono-substituted amino, di-substituted amino, thiohaloalkoxy, and alkylsulfone.

5. A compound of claim 1 wherein $R_{20}$, $R_{21}$, and $R_{24}$ are alkyl or substituted alkyl; ——— represents a bond present; and $R_{22}$ is hydroxy or an alkoxy group having 1 to 4 carbon atoms.

6. A compound of claim 1 having the formula:

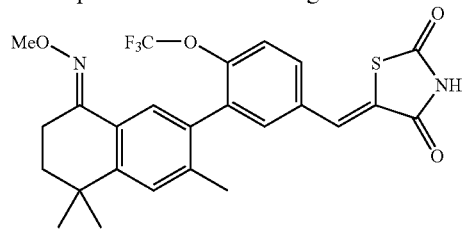

or a pharmaceutically acceptable salt thereof.

* * * * *

SEQUENCE LISTING

<160> NUMBER OF SEQ ID NOS: 3

<210> SEQ ID NO 1
<211> LENGTH: 462
<212> TYPE: PRT
<213> ORGANISM: Artificial Sequence
<220> FEATURE:
<223> OTHER INFORMATION: Description of Artificial Sequence; Note = synthetic construct

<400> SEQUENCE: 1

```
Met Asp Thr Lys His Phe Leu Pro Leu Asp Phe Ser Thr Gln Val Asn
 1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
```

```
                        340                 345                 350
Leu Val Ser Lys Met Arg Asp Met Gln Met Asp Lys Thr Glu Leu Gly
            355                 360                 365

Cys Leu Arg Ala Ile Val Leu Phe Asn Pro Asp Ser Lys Gly Leu Ser
        370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
            420                 425                 430

Leu Glu His Leu Phe Phe Lys Leu Ile Gly Asp Thr Pro Ile Asp
        435                 440                 445

Thr Phe Leu Met Glu Met Leu Glu Ala Pro His Gln Met Thr
450                 455                 460

<210> SEQ ID NO 2
<211> LENGTH: 533
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 2

Met Ser Trp Ala Ala Arg Pro Pro Phe Leu Pro Gln Arg His Ala Ala
1               5                   10                  15

Gly Gln Cys Gly Pro Val Gly Val Arg Lys Glu Met His Cys Gly Val
            20                  25                  30

Ala Ser Arg Trp Arg Arg Arg Pro Trp Leu Asp Pro Ala Ala Ala
        35                  40                  45

Ala Ala Ala Ala Val Ala Gly Gly Glu Gln Gln Thr Pro Glu Pro Glu
    50                  55                  60

Pro Gly Glu Ala Gly Arg Asp Gly Met Gly Asp Ser Gly Arg Asp Ser
65                  70                  75                  80

Arg Ser Pro Asp Ser Ser Pro Asn Pro Leu Pro Gln Gly Val Pro
                85                  90                  95

Pro Pro Ser Pro Pro Gly Pro Pro Leu Pro Pro Ser Thr Ala Pro Ser
            100                 105                 110

Leu Gly Gly Ser Gly Ala Pro Pro Pro Pro Met Pro Pro Pro Pro
        115                 120                 125

Leu Gly Ser Pro Phe Pro Val Ile Ser Ser Ser Met Gly Ser Pro Gly
130                 135                 140

Leu Pro Pro Pro Ala Pro Pro Gly Phe Ser Gly Pro Val Ser Ser Pro
145                 150                 155                 160

Gln Ile Asn Ser Thr Val Ser Leu Pro Gly Gly Gly Ser Gly Pro Pro
                165                 170                 175

Glu Asp Val Lys Pro Pro Val Leu Gly Val Arg Gly Leu His Cys Pro
            180                 185                 190

Pro Pro Pro Gly Gly Pro Gly Ala Gly Lys Arg Leu Cys Ala Ile Cys
        195                 200                 205

Gly Asp Arg Ser Ser Gly Lys His Tyr Gly Val Tyr Ser Cys Glu Gly
    210                 215                 220

Cys Lys Gly Phe Phe Lys Arg Thr Ile Arg Lys Asp Leu Thr Tyr Ser
225                 230                 235                 240
```

```
Cys Arg Asp Asn Lys Asp Cys Thr Val Asp Lys Arg Gln Arg Asn Arg
            245                 250                 255

Cys Gln Tyr Cys Arg Tyr Gln Lys Cys Leu Ala Thr Gly Met Lys Arg
            260                 265                 270

Glu Ala Val Gln Glu Glu Arg Gln Arg Gly Lys Asp Lys Asp Gly Asp
            275                 280                 285

Gly Glu Gly Ala Gly Ala Pro Glu Glu Met Pro Val Asp Arg Ile
290                 295                 300

Leu Glu Ala Glu Leu Ala Val Glu Gln Lys Ser Asp Gln Gly Val Glu
305                 310                 315                 320

Gly Pro Gly Gly Thr Gly Gly Ser Gly Ser Pro Asn Asp Pro Val
            325                 330                 335

Thr Asn Ile Cys Gln Ala Ala Asp Lys Gln Leu Phe Thr Leu Val Glu
            340                 345                 350

Trp Ala Lys Arg Ile Pro His Phe Ser Ser Leu Pro Leu Asp Asp Gln
            355                 360                 365

Val Ile Leu Leu Arg Ala Gly Trp Asn Glu Leu Leu Ile Ala Ser Phe
370                 375                 380

Ser His Arg Ser Ile Asp Val Arg Asp Gly Ile Leu Leu Ala Thr Gly
385                 390                 395                 400

Leu His Val His Arg Asn Ser Ala His Ser Ala Gly Val Gly Ala Ile
            405                 410                 415

Phe Asp Arg Val Leu Thr Glu Leu Val Ser Lys Met Arg Asp Met Arg
            420                 425                 430

Met Asp Lys Thr Glu Leu Gly Cys Leu Arg Ala Ile Ile Leu Phe Asn
            435                 440                 445

Pro Asp Ala Lys Gly Leu Ser Asn Pro Ser Glu Val Glu Val Leu Arg
            450                 455                 460

Glu Lys Val Tyr Ala Ser Leu Glu Thr Tyr Cys Lys Gln Lys Tyr Pro
465                 470                 475                 480

Glu Gln Gln Gly Arg Phe Ala Lys Leu Leu Leu Arg Leu Pro Ala Leu
            485                 490                 495

Arg Ser Ile Gly Leu Lys Cys Leu Glu His Leu Phe Phe Phe Lys Leu
            500                 505                 510

Ile Gly Asp Thr Pro Ile Asp Thr Phe Leu Met Glu Met Leu Glu Ala
            515                 520                 525

Pro His Gln Leu Ala
        530

<210> SEQ ID NO 3
<211> LENGTH: 463
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 3

Met Tyr Gly Asn Tyr Ser His Phe Met Lys Phe Pro Ala Gly Tyr Gly
  1               5                  10                  15

Gly Ser Pro Gly His Thr Gly Ser Thr Ser Met Ser Pro Ser Ala Ala
             20                  25                  30

Leu Ser Thr Gly Lys Pro Met Asp Ser His Pro Ser Tyr Thr Asp Thr
         35                  40                  45

Pro Val Ser Ala Pro Arg Thr Leu Ser Ala Val Gly Thr Pro Leu Asn
     50                  55                  60
```

-continued

```
Ala Leu Gly Ser Pro Tyr Arg Val Ile Thr Ser Ala Met Gly Pro Pro
 65                  70                  75                  80

Ser Gly Ala Leu Ala Ala Pro Pro Gly Ile Asn Leu Val Ala Pro Pro
                 85                  90                  95

Ser Ser Gln Leu Asn Val Val Asn Ser Val Ser Ser Ser Glu Asp Ile
                100                 105                 110

Lys Pro Leu Pro Gly Leu Pro Gly Ile Gly Asn Met Asn Tyr Pro Ser
                115                 120                 125

Thr Ser Pro Gly Ser Leu Val Lys His Ile Cys Ala Ile Cys Gly Asp
130                 135                 140

Arg Ser Ser Gly Lys His Tyr Gly Val Tyr Ser Cys Glu Gly Cys Lys
145                 150                 155                 160

Gly Phe Phe Lys Arg Thr Ile Arg Lys Asp Leu Ile Tyr Thr Cys Arg
                165                 170                 175

Asp Asn Lys Asp Cys Leu Ile Asp Lys Arg Gln Arg Asn Arg Cys Gln
                180                 185                 190

Tyr Cys Arg Tyr Gln Lys Cys Leu Val Met Gly Met Lys Arg Glu Ala
                195                 200                 205

Val Gln Glu Glu Arg Gln Arg Ser Arg Glu Arg Ala Glu Ser Glu Ala
210                 215                 220

Glu Cys Ala Thr Ser Gly His Glu Asp Met Pro Val Glu Arg Ile Leu
225                 230                 235                 240

Glu Ala Glu Leu Ala Val Glu Pro Lys Thr Glu Ser Tyr Gly Asp Met
                245                 250                 255

Asn Met Glu Asn Ser Thr Asn Asp Pro Val Thr Asn Ile Cys His Ala
                260                 265                 270

Ala Asp Lys Gln Leu Phe Thr Leu Val Glu Trp Ala Lys Arg Ile Pro
                275                 280                 285

His Phe Ser Asp Leu Thr Leu Glu Asp Gln Val Ile Leu Leu Arg Ala
                290                 295                 300

Gly Trp Asn Glu Leu Leu Ile Ala Ser Phe Ser His Arg Ser Val Ser
305                 310                 315                 320

Val Gln Asp Gly Ile Leu Leu Ala Thr Gly Leu His Val His Arg Ser
                325                 330                 335

Ser Ala His Ser Ala Gly Val Gly Ser Ile Phe Asp Arg Val Leu Thr
                340                 345                 350

Glu Leu Val Ser Lys Met Lys Asp Met Gln Met Asp Lys Ser Glu Leu
                355                 360                 365

Gly Cys Leu Arg Ala Ile Val Leu Phe Asn Pro Asp Ala Lys Gly Leu
                370                 375                 380

Ser Asn Pro Ser Glu Val Glu Thr Leu Arg Glu Lys Val Tyr Ala Thr
385                 390                 395                 400

Leu Glu Ala Tyr Thr Lys Gln Lys Tyr Pro Glu Gln Pro Gly Arg Phe
                405                 410                 415

Ala Lys Leu Leu Leu Arg Leu Pro Ala Leu Arg Ser Ile Gly Leu Lys
                420                 425                 430

Cys Leu Glu His Leu Phe Phe Lys Leu Ile Gly Asp Thr Pro Ile
                435                 440                 445

Asp Thr Phe Leu Met Glu Met Leu Glu Thr Pro Leu Gln Ile Thr
450                 455                 460
```